(12) United States Patent
Akita

(10) Patent No.: US 9,386,920 B2
(45) Date of Patent: Jul. 12, 2016

(54) OPHTHALMOLOGIC IMAGE PROCESSING APPARATUS

(71) Applicant: NIDEK CO., LTD., Aichi (JP)

(72) Inventor: Junichi Akita, Aichi (JP)

(73) Assignee: NIDEK CO., LTD., Aichi (JP)

( * ) Notice: Subject to any disclaimer, the term of this patent is extended or adjusted under 35 U.S.C. 154(b) by 0 days.

(21) Appl. No.: 14/499,557

(22) Filed: Sep. 29, 2014

(65) Prior Publication Data

US 2015/0092161 A1  Apr. 2, 2015

(30) Foreign Application Priority Data

Sep. 30, 2013  (JP) ................................. 2013-204143
Sep. 30, 2013  (JP) ................................. 2013-204144
Oct. 31, 2013  (JP) ................................. 2013-226374

(51) Int. Cl.
*A61B 3/14* (2006.01)
*A61B 3/10* (2006.01)
*A61B 3/00* (2006.01)
*A61B 3/12* (2006.01)

(52) U.S. Cl.
CPC ............. *A61B 3/0058* (2013.01); *A61B 3/0025* (2013.01); *A61B 3/12* (2013.01); *A61B 3/14* (2013.01)

(58) Field of Classification Search
USPC ................................................. 351/200–246
See application file for complete search history.

(56) References Cited

U.S. PATENT DOCUMENTS

| 2008/0225226 | A1 | 9/2008 | Fujishiro et al. |
| 2009/0073386 | A1 | 3/2009 | Purcell |
| 2010/0277692 | A1 | 11/2010 | Mukai |
| 2012/0220850 | A1* | 8/2012 | Umekawa ............ A61B 3/0041 600/401 |
| 2012/0249769 | A1* | 10/2012 | Naba ....................... A61B 3/102 348/78 |
| 2012/0249957 | A1 | 10/2012 | Hanebuchi |
| 2012/0253183 | A1* | 10/2012 | Muto ...................... G06T 19/00 600/425 |
| 2014/0185009 | A1 | 7/2014 | Imamura |
| 2014/0185889 | A1 | 7/2014 | Yonezawa |

FOREIGN PATENT DOCUMENTS

| EP | 2505128 A1 | 10/2012 |
| EP | 2749204 A1 | 7/2014 |
| EP | 2749205 A1 | 7/2014 |
| JP | 2008-228781 | 10/2008 |
| JP | 2009-011381 | 1/2009 |

OTHER PUBLICATIONS

Extended European Search Report dated Jan. 28, 2015 issued in the corresponding European patent application No. 14186978.4.

* cited by examiner

*Primary Examiner* — Mohammed Hasan
(74) *Attorney, Agent, or Firm* — Rankin, Hill & Clark LLP

(57) ABSTRACT

An ophthalmic image processing apparatus includes: a storage unit configured to store a fundus image and a first partial image, the first partial image being a partial image photographed for a part of the fundus image and having a higher resolution than the fundus image; and a display control unit configured to combine the first partial image with respect to an image region on the fundus image corresponding to the first partial image, and to display a combined image of the fundus image and the first partial image on a display medium.

19 Claims, 15 Drawing Sheets

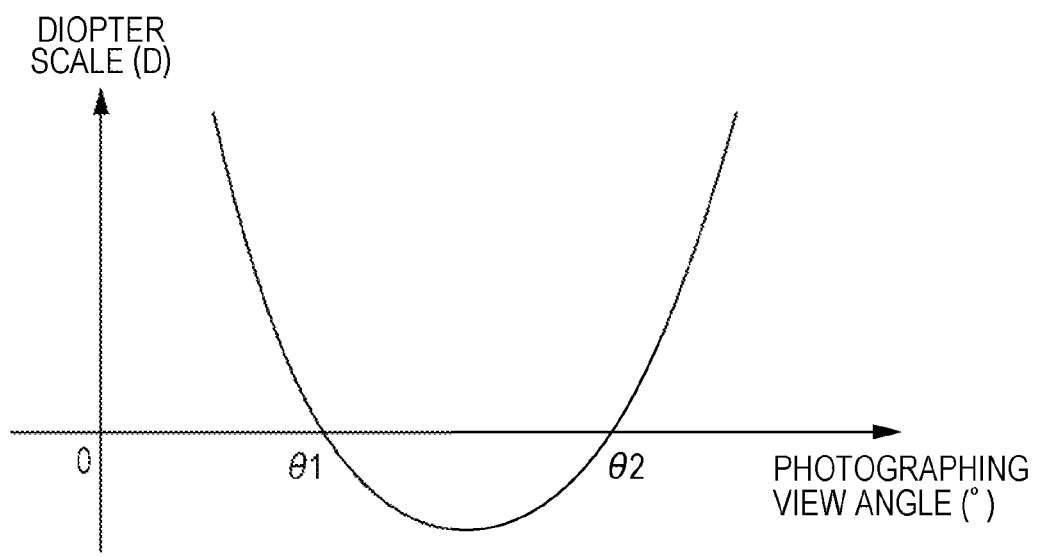

FIG. 4

| | NARROW-ANGLE PHOTOGRAPHY MODE (PHOTOGRAPHING VIEW ANGLE APPROX. 50°) | WIDE-ANGLE PHOTOGRAPHY MODE (PHOTOGRAPHING VIEW ANGLE APPROX. 110°) |
|---|---|---|
| FOCAL LENGTH OF FIRST CONCAVE LENS | 42.6mm | |
| FOCAL LENGTH OF SECOND CONCAVE LENS | 70.5mm | |
| DISTANCE FROM SCANNING UNIT TO SECOND CONCAVE LENS | 115.3mm | 177.1mm |
| DISTANCE FROM SECOND CONCAVE LENS TO FIRST CONCAVE LENS | 66.5mm | 4.8mm |
| DISTANCE FROM FIRST CONCAVE LENS TO TURNING POINT | 31.1mm | 30.9mm |
| DISTANCE FROM SCANNING UNIT TO TURNING POINT | 212.9mm | 212.8mm |
| DIOPTER SCALE | 0D | 0D |

(PHOTOGRAPHY DISPLAY PROCESS)

OPHTHALMOLOGIC IMAGE PROCESSING APPARATUS

CROSS-REFERENCE TO RELATED APPLICATION

This application claims priority from Japanese Patent Application Nos. 2013-204143 and 2013-204144 filed on Sep. 30, 2013 and 2013-226374 filed on Oct. 31, 2013 with the Japan Patent Office, the entire contents of which are hereby incorporated by reference.

BACKGROUND

1. Technical Field

The present disclosure relates to an ophthalmic image processing apparatus.

2. Related Art

Conventionally, a scanning laser ophthalmoscope has been known as one type of fundus photographing apparatus. The scanning laser ophthalmoscope scans the fundus with a laser beam emitted from a light source by pivoting the laser beam about a point near the pupil, and the fundus reflected light is received to obtain a fundus image.

The above device acquires a wide-angle image using, for example, a wide-angle attachment (see JP-A-209-011381).

Some fundus photographing apparatuses can display a live image including a plurality of continuous fundus images (see JP-A-2008-228781), enabling an examiner to recognize the state of the fundus, for example, by observing the live image.

SUMMARY

An ophthalmic image processing apparatus includes: a storage unit configured to store a fundus image and a first partial image, the first partial image being a partial image photographed for a part of the fundus image and having a higher resolution than the fundus image; and a display control unit configured to combine the first partial image with respect to an image region on the fundus image corresponding to the first partial image, and to display a combined image of the fundus image and the first partial image on a display medium.

BRIEF DESCRIPTION OF DRAWINGS

FIG. 3 is a graph schematically illustrating the relationship between the photographing view angle and the diopter scale (D) by the objective lens optical system under the condition of a constant position of a pivot point with respect to the examinee's eye;

FIG. 4 is a table showing design values of the objective lens optical system for maintaining the position of the pivot point with respect to the examinee's eye and the diopter scale of the photographing optical system before and after the photographing view angle is switched between the first view angle and the second view angle;

DETAILED DESCRIPTION

Figure 1:
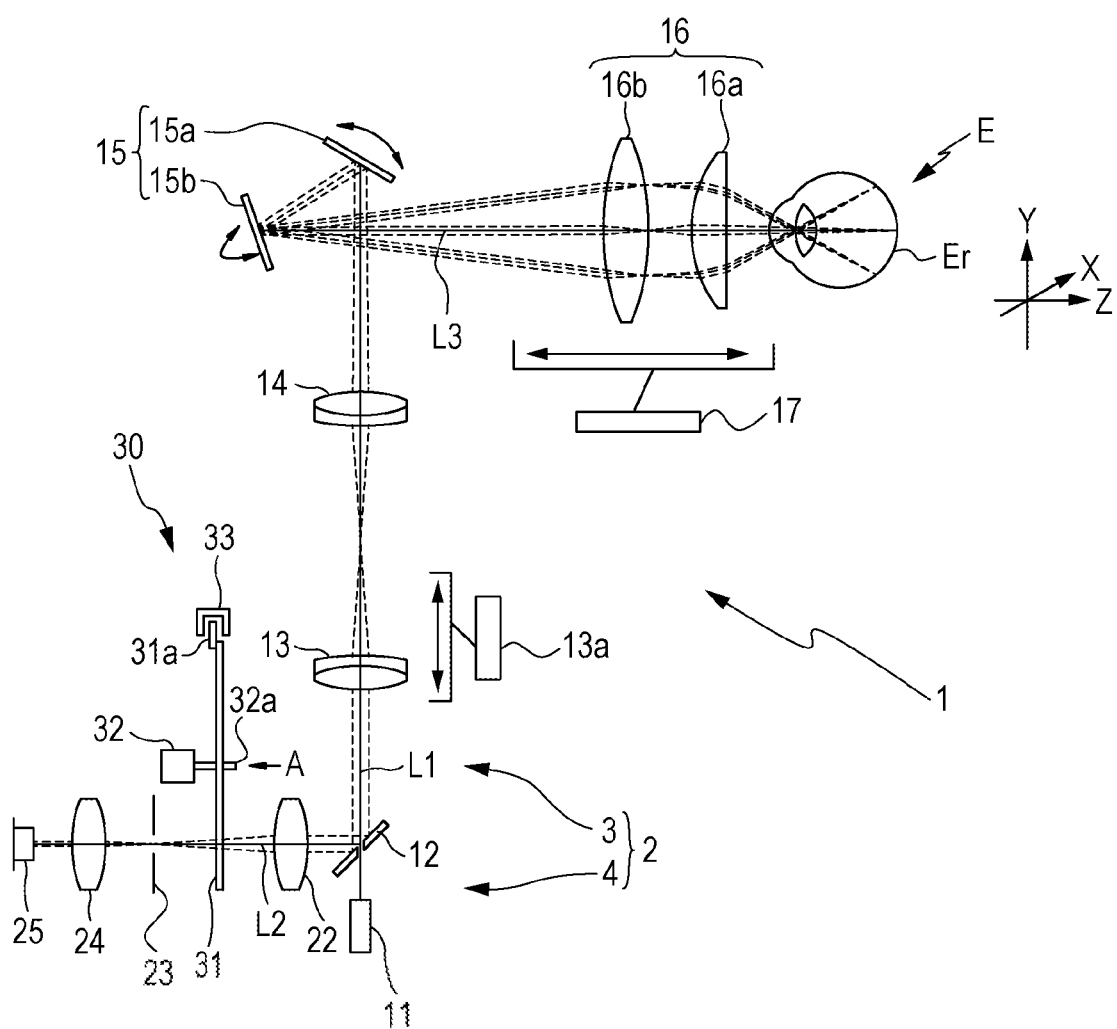
FIG. 1 is a schematic diagram illustrating the configuration of an optical system included in an ophthalmologic photographing apparatus according to a first embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In a fundus photographing apparatus, the resolution of an image photographed by the device and the photographing range on the fundus have a trade-off relationship. For example, when a wide area of the fundus is photographed using a wide-angle attachment, the photographing magnification decreases, so that the resolution is relatively lowered. Namely, the image obtained by wide-area photography is not suitable for confirmation of a detailed portion. On the other hand, when the fundus is photographed by limiting the photographing range, the photographing magnification increases, thus ensuring resolution. However, the image obtained at a high magnification ratio is not suitable for overall observation.

When the entire fundus image is displayed as a live image, a feature area present in a part of the fundus, such as a lesioned part, may become inconspicuous, making it difficult for the examiner to perform detailed observation of the feature area. On the other hand, when only a part of the fundus image is displayed as the live image, observation of the feature area present in that part by the examiner becomes easy. However, from the live image in which only a part of the fundus image is displayed, the entirety of the fundus image cannot be confirmed. As a result, the examiner may overlook the lesioned part or the like present in the photographing range of the fundus image, for example.

An object of an embodiment of the present disclosure is to provide an ophthalmic image processing apparatus that enables the examiner to better recognize the state of the fundus through an image displayed on a display medium.

An ophthalmic image processing apparatus according to a first aspect of the present disclosure includes: a storage unit configured to store a fundus image and a first partial image, the first partial image being a partial image photographed for a part of the fundus image and having a higher resolution than the fundus image; and a display control unit configured to combine the first partial image with respect to an image region on the fundus image corresponding to the first partial image, and to display a combined image of the fundus image and the first partial image on a display medium.

An ophthalmic image processing apparatus according to a second aspect of the present disclosure includes: a photographing optical system configured to photograph a fundus image by projecting light to the fundus of an examinee's eye and receiving light from the fundus as a result of the light projection using a light receiving device; and a display control unit configured to generate the fundus image and a second partial image as an image of a part extracted from the fundus image, based on a light receiving signal from the light receiving device, and to display a first live image including a plurality of continuous fundus images and a second live image including a plurality of continuous second partial images side by side on a display medium.

An ophthalmic image processing apparatus according to a third aspect of the present disclosure includes: a photographing optical system configured to photograph a fundus image by projecting light to the fundus of an examinee's eye and receiving light from the fundus as a result of the light projection using a light receiving device; and a display control unit configured to display the fundus image photographed using the photographing optical system and a second partial image photographed for a range of interest included in the fundus image on a display medium, and to display at least one of the fundus image and the second partial image as a live image.

According to an aspect of the present disclosure, the photographing view angle can be changed to successfully photograph an image of the fundus.

In the following, typical embodiments of the present disclosure will be described with reference to the drawings. First, a first embodiment will be described with reference to FIGS. 1 to 9.

FIG. 1 illustrates an optical system included in an ophthalmologic photographing apparatus 1 according to the first embodiment. In the first embodiment, the ophthalmologic photographing apparatus 1 includes a scanning laser ophthalmoscope (SLO) as a basic configuration. The ophthalmologic photographing apparatus 1 may be a device integrated with another ophthalmic apparatus, such as an optical coherence tomography (OCT) or a campimeter.

As an example, the ophthalmologic photographing apparatus 1 is mainly provided with a photographing optical system 2. The ophthalmologic photographing apparatus 1 according to the first embodiment is also provided with a rotating plate unit 30. The photographing optical system 2 will be described. The photographing optical system 2 projects light to the fundus Er of the examinee's eye E, while receiving light emitted from each position of the fundus Er in association with the projected light, using a light receiving device 25. While the details will be described later, the ophthalmologic photographing apparatus 1 acquires (photographs) a fundus image based on the result of light reception by the light receiving device 25. The photographing optical system 2 includes a light projecting optical system 3 and a light receiving optical system 4. The photographing optical system 2 is moved by a drive mechanism 50 (see FIG. 7), which will be described later, in the right/left direction (arrow X direction), the up/down direction (arrow Y direction), and front/rear direction (arrow Z direction) of the examinee's eye E.

The light projecting optical system 3 projects light (illuminating light or excitation light) to each position in the photographing range of the fundus Er of the examinee's eye E. In the first embodiment, the light projecting optical system 3 includes a laser beam emitting portion 11, an apertured mirror 12, a lens 13, a lens 14, a scanning unit 15, and, an objective lens optical system 16.

The laser beam emitting portion 11 is a light source for the photographing optical system 2. The laser beam emitting portion 11 may emit, for example, at least a laser beam of a first wavelength (of approximately 790 nm in wavelength) and a laser beam of a second wavelength (approximately 490 nm in wavelength). Obviously, the laser beam emitting portion 11 may emit only monochromatic light. In the first embodiment, the laser beam emitting portion 11 may be configured to emit two kinds of laser beam simultaneously, or only one thereof.

The laser beam from the laser beam emitting portion 11 passes through the opening portion of the apertured mirror 12 having the opening portion at the center, is transmitted through the lens 13 and lens 14, and then travels toward the scanning unit 15. The light flux reflected by the scanning unit 15 passes through the objective lens optical system 16, and is then condensed at the fundus Er of the examinee's eye E. As the fundus Er is irradiated with the laser beam from the laser beam emitting portion 11, the fundus Er emits light. For example, the laser beam is scattered or reflected by the fundus Er. The light scattered or reflected by the fundus Er (hereafter referred to as "fundus reflected light") is emitted from the pupil. The laser beam may also excite a fluorescence substance present in the fundus Er, and fluorescence emitted from the fluorescence substance present in the fundus Er may be emitted from the pupil.

In the first embodiment, the lens 13 is configured to be movable by a drive mechanism 13a in the optical axis L1 direction. Depending on the position of the lens 13, the diopter scale of the photographing optical system 2 is varied. Thus, in the first embodiment, a diopter scale error of the examinee's eye E with respect to the emmetropic eye is corrected (mitigated) by adjusting the position of the lens 13. The diopter scale error of the examinee's eye E may be corrected by displacing the lens 14.

The scanning unit 15 is a unit for varying the direction of travel of (i.e., deflect) the laser beam guided from the laser beam emitting portion 11 so as to scan the fundus with the laser beam. In the first embodiment, the scanning unit 15 includes a resonant scanner 15a and a galvanometer mirror 15b.

As the scanning unit 15, an acousto-optic modulator (AOM) or the like for changing (deflecting) the direction of travel of light may be used, as well as the reflective mirror (such as a galvanometer mirror, a polygon mirror, or a resonant scanner).

In the first embodiment, the resonant scanner 15a deflects the laser beam projected to the fundus of the examinee's eye E in a predetermined direction. As illustrated in FIG. 1, the light that has passed through the resonant scanner 15a travels toward the galvanometer mirror 15b. In the first embodiment, the resonant scanner 15a is rotated by the motor 15c (see FIG. 7), whereby the laser beam irradiation position (scan position) on the fundus Er is moved in the horizontal direction (i.e., X direction).

Further in the first embodiment, the galvanometer mirror 15b further deflects the laser beam that has passed through the resonant scanner 15a in a different direction from the resonant scanner 15a. As illustrated in FIG. 1, the light that has passed through the galvanometer mirror 15b travels toward the objective lens optical system 16. In the first embodiment, the galvanometer mirror 15b is rotated by the motor 15d (see FIG. 7), whereby the laser beam irradiation position on the fundus Er is moved in the vertical direction (i.e., Y direction).

Thus, the scanning unit 15 according to the first embodiment scans the fundus Er two-dimensionally with the laser beam by the X-direction scanning of the fundus Er using the resonant scanner 15a and the Y-direction scanning using the galvanometer mirror 15b.

The objective lens optical system 16 guides the laser beam that has passed through the scanning unit 15 through the pupil position. In the first embodiment, the objective lens optical system 16 includes a first convex lens 16a and a second convex lens 16b. As illustrated in FIG. 1, in the objective lens optical system 16, these lenses are disposed in series. The number of the lenses in the objective lens optical system 16 is not limited to the above configuration, and the objective lens optical system 16 may be an objective lens system having three or more lenses. Each of the lenses of the objective lens optical system 16 may be an aspherical lens or a compound lens including a plurality of lenses, for example, as needed for aberration correction.

The first convex lens 16a is disposed nearest the examinee's eye among the lenses of the objective lens optical system 16. The second convex lens 16b is disposed closer to the scanning unit 15 than the first convex lens 16a. As illustrated in FIG. 1, in the first embodiment, a piano-convex lens with the convex surface facing the scanning unit 15 side is used as the first convex lens 16a. As the second convex lens 16b, a biconvex lens is used. However, these lens shapes are merely exemplary, and the lenses only need to have positive powers.

In the first embodiment, the laser beam that has passed the objective lens optical system 16 travels through a point (hereafter referred to as "pivot point") on the optical axis L3 of the objective lens optical system 16 and irradiates the fundus Er. In the first embodiment, the position of the pivot point is optically conjugate with the scanning unit 15 (such as an intermediate point of the resonant scanner 15a and the galvanometer mirror 15b) through the objective lens optical system 16. Thus, a principal ray of the laser beam that has passed through the objective lens optical system 16 is pivoted about the pivot point in accordance with the operation of the scanning unit 15. As a result, the fundus Er is two-dimensionally scanned by the laser beam. By aligning the pivot point of the laser beam and the pupil position of the examinee's eye E in advance, being eclipsed by the iris is suppressed, allowing the laser beam to be guided to the fundus in a preferable manner. As a result, the fundus image can be photographed in a preferable manner.

The ophthalmologic photographing apparatus 1 according to the first embodiment also includes a lens moving mechanism (a view angle switch mechanism, or a photographing view angle adjustment mechanism) 17 that moves each lens of the objective lens optical system 16. The lens moving mechanism 17 can move each lens of the objective lens optical system 16 by an arbitrary amount of movement. In the first embodiment, the lens moving mechanism 17 is described as a stand-alone device. However, this is merely for the sake of description, and the configuration of the lens moving mechanism 17 is not limited to the above. For example, as the lens moving mechanism 17, a plurality of devices each configured to move one lens may be used.

Figure 2A:
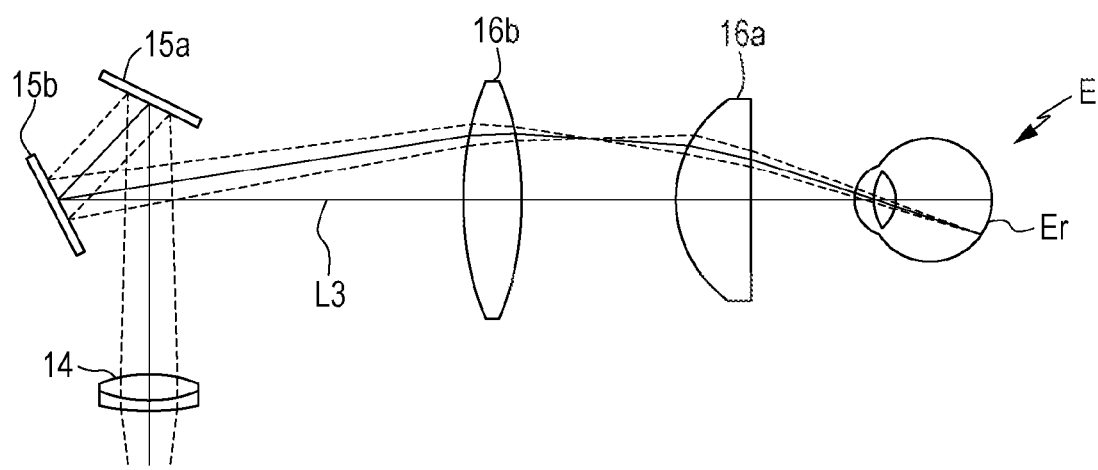
FIG. 2A is a schematic diagram illustrating an objective lens optical system in a narrow-angle photography mode.
Figure 2B:
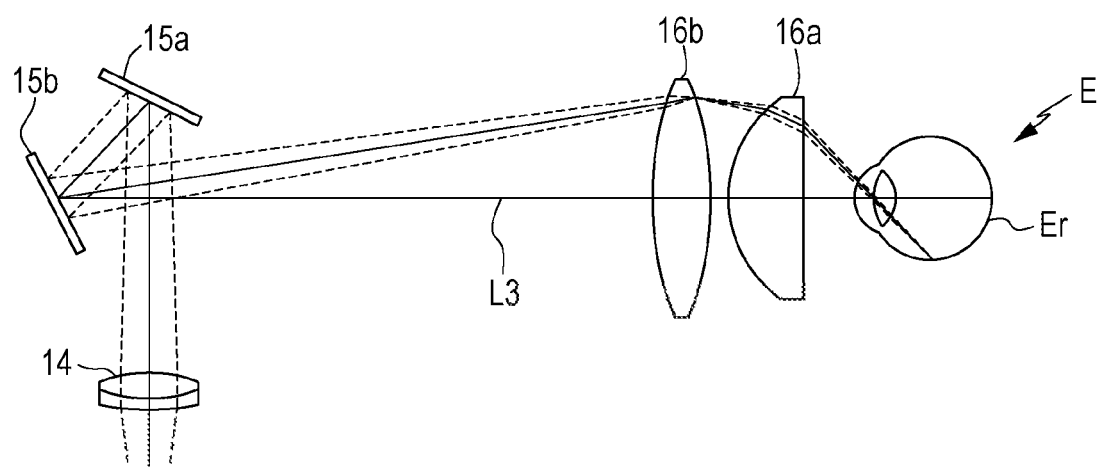
FIG. 2B is a schematic diagram of the objective lens optical system in a wide-angle photography mode.

In the first embodiment, the location of each lens in the objective lens optical system 16 is modified by the lens moving mechanism 17, whereby the range of irradiation by the laser beam projected from the light projecting optical system 3, i.e., the photographing view angle in the ophthalmologic photographing apparatus 1 (or the photographing optical system 2) is modified. The ophthalmologic photographing apparatus 1 according to the first embodiment is configured to switch the photographing view angle at least between the two types, namely a first view angle and a second view angle wider than the first view angle. FIG. 2A illustrates the location of each of the lenses 16a and 16b when the photographing view angle is the first view angle in the first embodiment. FIG. 2B illustrates the location of each of the lenses 16a and 16b when the photographing view angle is the second view angle in the first embodiment. In the following, the state of the ophthalmologic photographing apparatus 1 when the photographing view angle is the first view angle will be referred to as a narrow-angle photography mode. The state of the ophthalmologic photographing apparatus 1 when the photographing view angle is the second view angle will be referred to as a wide-angle photography mode.

As illustrated in FIGS. 2A and 2B, in the first embodiment, each lens of the objective lens optical system 16 is disposed by a control unit 90 which will be described later so that the position of the pivot point and the like with respect to the ophthalmologic photographing apparatus 1 will be maintained even when the laser beam irradiation range is modified. For example, in the first embodiment, the first convex lens 16a and the second convex lens 16b are displaced in the same direction along the optical axis L3, whereby the photographing view angle is mutually modified to the first view angle and the second view angle (see FIG. 2A and FIG. 2B).

For example, in the first embodiment, when the photographing view angle is increased from the first view angle to the second view angle, the two convex lenses 16a and 16b are both moved closer to the examinee's eye E along the optical axis L3 (FIG. 2A to FIG. 2B). In the first embodiment, the second convex lens 16b is moved more greatly than the first convex lens 16a. Namely, when the photographing view angle is the second view angle, the two convex lenses 16a and 16b are moved such that their lens interval becomes narrow compared with when the photographing view angle is the first view angle. In this way, when the photographing view angle is the second view angle, the incidence height of the laser beam incident on the convex lenses 16a and 16b becomes greater than when the photographing view angle is the first view angle. As a result, when the photographing view angle is the second view angle, the converging action of the two convex lenses 16a and 16b becomes greater than when the photographing view angle is the first view angle, whereby the photographing view angle is increased compared with the first view angle. Furthermore, in the first embodiment, in order to set the photographing view angle to the second view angle, the first convex lens 16a is moved by a smaller displacement than for the second convex lens 16b. Thus, the pivot point is brought closer to the first convex lens 16a than when the photographing view angle is the first view angle. As a result, in the present device, the position of the pivot point with respect to the examinee's eye is maintained before and after the photographing view angle is switched from the first view angle to the second view angle.

On the other hand, in the first embodiment, when the photographing view angle is narrowed from the second view angle to the first view angle, each lens of the objective lens optical system 16 is moved in the opposite direction from when the photographing view angle is increased (FIG. 2B to FIG. 2A). As a result, when the photographing view angle is the first view angle, the incidence height of the laser beam incident on the two convex lenses 16a and 16b is lowered compared with when the photographing view angle is the second view angle. In this way, when the photographing view angle is the first view angle, the converging action of each of the convex lenses 16a and 16b becomes smaller than when the photographing view angle is the second view angle, whereby the photographing view angle becomes narrower than the second view angle. At this time, in order to set the photographing view angle to the first view angle, the first convex lens 16*a* is moved toward the scanning unit 15 by a smaller amount of displacement than for the second convex lens 16*b*. Thus, the pivot point is located far from the first convex lens 16*a* compared with when the photographing view angle is the second view angle. As a result, in the present device, the position of the pivot point with respect to the examinee's eye is maintained before and after the photographing view angle is switched from the second view angle to the first view angle.

Thus, in the ophthalmologic photographing apparatus 1 according to the first embodiment, the position of the pivot point of the laser beam with respect to the examinee's eye is maintained between when the photographing view angle is the first view angle and when the angle is the second view angle. Accordingly, when the photographing view angle is varied, the need for readjusting the positional relationship between the device and the examinee's eye E so as to position the pivot point near the pupil of the examinee's eye E can be decreased. Namely, the ophthalmologic photographing apparatus 1 according to the first embodiment can photograph fundus images with different photographing view angles with the positional relationship between the examinee's eye E and the device constantly maintained. Thus, the ophthalmologic photographing apparatus 1 according to the first embodiment can photograph fundus images with different photographing view angles in a preferable manner.

Under the condition that the position of the pivot point with respect to the examinee's eye is constantly maintained, the diopter scale of the photographing optical system 2 is changed in accordance with the photographing view angle of the objective lens optical system 16. The diopter scale (D) corresponding to each photographing view angle when the position of the pivot point is constant is schematically shown in the graph of FIG. 3. Namely, in the graph with the vertical axis showing the diopter scale (D) and the horizontal axis showing the photographing view angle, the diopter scale (D) corresponding to each photographing view angle is shown by the downwardly stretched curve with a negative value (D) as the minimum value. As illustrated in FIG. 3, the objective lens optical system 16 including the two convex lenses 16*a* and 16*b* have the same diopter scale (D) at the mutually different two photographing view angles. For example, the diopter scale by the objective lens optical system 16 is 0 (D) when the photographing view angle is $\theta1$ and $\theta2$ ($\theta1<\theta2$).

Thus, in the ophthalmologic photographing apparatus 1, the first view angle and the second view angle may be set such that the diopter scale in the narrow-angle photography mode (i.e., when the photographing view angle is the first view angle; see FIG. 2A), and the diopter scale in the wide-angle photography mode (i.e., when the photographing view angle is the second view angle; see FIG. 2B) have a constant value (such as 0 (D)). In this case, in the ophthalmologic photographing apparatus (ophthalmic apparatus) 1, when the photographing view angle is switched between the first view angle and the second view angle, the two convex lenses 16*a* and 16*b* are disposed by the lens moving mechanism 17 so that the diopter scale of the photographing optical system 2 as well as the position of the pivot point with respect to the examinee's eye is maintained.

FIG. 4 illustrates an example of the focal point distance of the convex lenses 16*a* and 16*b* and the location of the convex lenses 16*a* and 16*b* such that diopter scale and the position of the pivot point can be maintained when the photographing view angle is switched between the first view angle of approximately 50° and the second view angle of approximately 110°. In the example of FIG. 4, the focal point distance of the first convex lens 16*a* is 42.6 mm, and the focal point distance of the second convex lens 16*b* is 70.5 mm.

When the photographing view angle is the first view angle (approximately 50°), the second convex lens 16*b* is located 115.3 mm away from the scanning unit 15 (in the first embodiment, the intermediate point of the resonant scanner 15*a* and the galvanometer mirror 15*b*) toward the examinee's eye E. The first convex lens 16*a* is located further 66.5 mm away from the second convex lens 16*b* toward the examinee's eye E. As a result, the position of the pivot point is 31.1 mm away from the first convex lens 16*a* toward the examinee's eye E. Namely, when the photographing view angle is 50°, the distance from the scanning unit 15 to the pivot point is 212.9 mm. Also, the diopter scale by the objective lens optical system 16 becomes 0 (D).

On the other hand, when the photographing view angle is the second view angle (approximately 110°), the second convex lens 16*b* is located 177.1 mm away from the scanning unit 15 toward the examinee's eye E. The first convex lens 16*a* is located further 4.8 mm away from the second convex lens 16*b* toward the examinee's eye E. As a result, the position of the pivot point is 30.9 mm away from the first convex lens 16*a* toward the examinee's eye E. Namely, when the photographing view angle is 110°, the distance from the scanning unit 15 to the pivot point is 212.8 mm.

Thus, in the example of FIG. 4, the distance from the scanning unit 15 to the pivot point is substantially the same when the photographing view angle is the first view angle (approximately 50°) and when the photographing view angle is the second view angle (approximately 110°). When the convex lenses 16*a* and 16*b* are located as described above so that the photographing view angle is the second view angle (approximately 110°), the diopter scale of the objective lens optical system 16 is 0 (D). Thus, in the example of FIG. 4, the diopter scale of the photographing optical system 2 is maintained between when the photographing view angle is the first view angle (approximately 50°) and when the photographing view angle is the second view angle (approximately 110°). The diopter scale maintained when the photographing view angle is modified may not be 0 (D). For example, the parameters shown in FIG. 4 may be set such that the diopter scale at the first view angle and the second view angle is −2D. The focal point distances and specific positions of the respective lenses 16*a* and 16*b* are not limited to those of the illustrated example of FIG. 4. The focal point distances and specific positions of the respective lenses 16*a* and 16*b* may be determined as needed in accordance with the photographing view angle and the like that is set.

Thus, before and after the photographing view angle is switched between the first view angle and the second view angle, the diopter scale of the photographing optical system 2 as well as the position of the pivot point with respect to the examinee's eye is maintained. In this way, the need for adjusting the diopter scale after the photographing view angle is switched is decreased. Therefore, fundus images with different photographing view angles can be obtained in a more preferable manner.

The ophthalmologic photographing apparatus 1 may be configured such that the diopter scale of the photographing optical system 2 is not maintained when the photographing view angle is switched between the first view angle and the second view angle. In this case, the ophthalmologic photographing apparatus 1 may utilize a diopter scale correction mechanism provided to the photographing optical system 2. More specifically, the change in diopter scale as a result of switching of the photographing view angle between the first view angle and the second view angle may be corrected by displacing at least one lens (such as the lens 13) on the common optical path of the light projecting optical system 3 and the light receiving optical system 4. When the diopter scale change is corrected by displacing the lens 13, the lens 13 and the drive mechanism 13a function as the diopter scale correction mechanism.

In the first embodiment, the photographing view angle in the photographing optical system 2 is switched by moving the lenses of the objective lens optical system 16 using the lens moving mechanism 17. Alternatively, the ophthalmologic photographing apparatus 1 may be provided with a plurality of objective lens optical systems for setting mutually different photographing view angles in the photographing optical system 2, and a view angle switch mechanism for alternatively locating one of the plurality of objective lens optical systems on the optical path of the laser beam. It is noted, however, that a more compact configuration may be obtained by the device that, as according to the first embodiment, moves the position of the lenses included in one optical system (such as the respective lenses of the objective lens optical system 16 in the first embodiment) than a device that switches the photographing view angle by switching the objective lens optical system disposed forwardly of the examinee's eye E.

The light receiving optical system 4 will be described. The light receiving optical system 4 receives the light from the fundus Er (i.e., fundus reflected light in the case of normal photography, or fluorescence produced in the fundus Er in the case of fluorescence photography) accompanying the projection of laser beam from the light projecting optical system 3. The light receiving optical system 4 according to the first embodiment shares with the light projecting optical system 3 the members from the apertured mirror 12 to the objective lens optical system 16 disposed on the optical axis (optical path) L1 of the light projecting optical system 3. The light receiving optical system 4 according to the first embodiment includes a lens 22, a pinhole plate 23, a lens 24, and a light receiving device 25.

When the fundus of the examinee's eye E is irradiated with laser beam, the light reflected by or emitted from the fundus Er based on the laser beam travels back along the light projecting optical system 3 and is reflected by the apertured mirror 12, thus being guided to the lens 22. The pupil position of the examinee's eye E and the opening portion of the apertured mirror 12 have an optically conjugate relationship. Downstream of the lens 22, the light from the fundus Er has a focal point at the pinhole of the pinhole plate 23, and is received by the light receiving device 25 via the lens 24. In the first embodiment, as the light receiving device 25, an avalanche photodiode (APD) having sensitivity in the visible range and infrared range is used.

The rotating plate unit 30 selects the wavelength of the light received by the light receiving device 25. The rotating plate unit 30 includes a rotating plate 31, a pulse motor 32, and a sensor 33.

Figure 5:
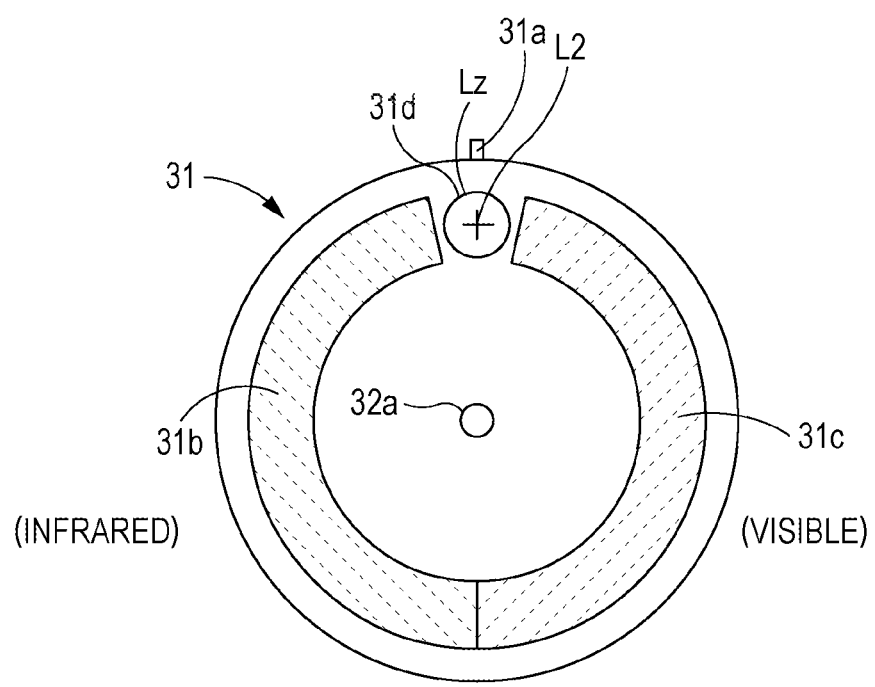
FIG. 5 is a diagram illustrating a rotating plate as viewed from the direction of arrow A in FIG. 1.
Figure 6A:
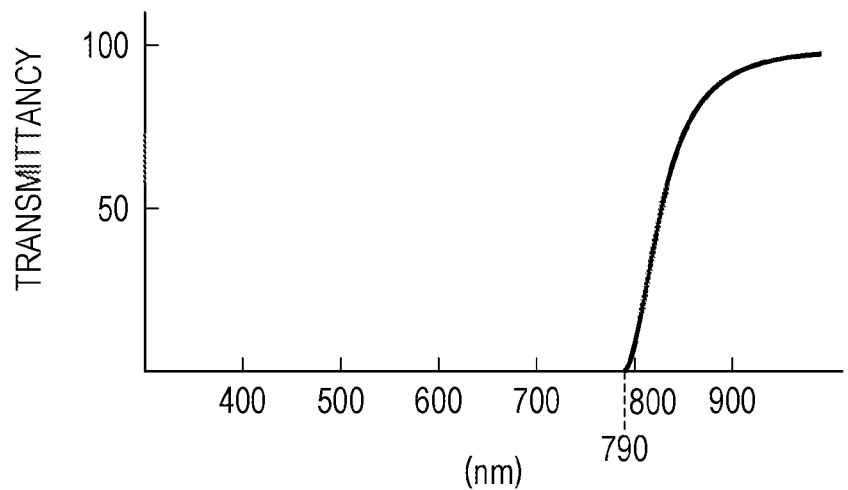
FIGS. 6A and 6B are graphs illustrating filtering characteristics of a filter included in the rotating plate.
Figure 6B:
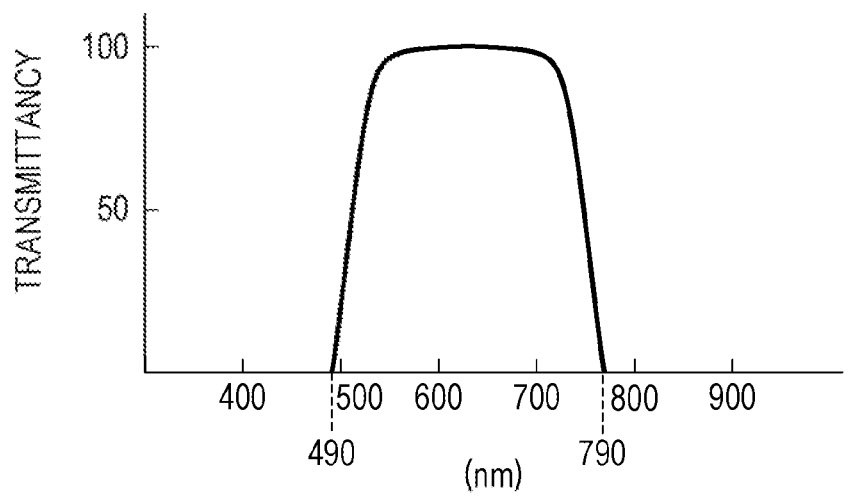

The rotating plate 31 includes a plurality of types of barrier filters for observing the fluorescence produced in the fundus Er. The rotating plate 31 is placed with the plate surface of the rotating plate 31 being orthogonal to the optical axis L2. The optical axis L2 of the light receiving optical system 4 passes through a part of the rotating plate 31 away from its rotating axis. The rotating plate 31 is rotated by the pulse motor 32. As illustrated in FIG. 5, the rotating plate 31 is provided with a filter 31b, a filter 32c, and an opening portion 31d. The filter 31b, the filter 32c, and the opening portion 31d are disposed on the trajectory that a photography region Lz of the light receiving optical system 4 follows as the rotating plate 31 is rotated. Thus, as the rotating plate 31 is rotated, any of the filter 31b, the filter 32c, and the opening portion 31d is set in the photography region Lz of the light receiving optical system 4. In the rotating plate 31, the type of the filter that is set, for example, is adjusted based on the rotation angle detected by the sensor 33.

The filter 31b is a barrier filter for infrared fluorescence photography. The filter 31b has spectral characteristics shown in FIG. 6A. The filter 31b may be used for indocyanine-green-fundus-angiography (ICG), which is a type of infrared fluorescence photography. ICG is fluorescence photography that uses indocyanine green as the fluorescence fundus contrast agent. In the ophthalmologic photographing apparatus 1 according to the first embodiment, first light (wavelength around 790 nm) is irradiated from the laser beam emitting portion 11 to perform photography. ICG is mainly used for observation of a choroid blood vessel.

The filter 31c is a barrier filter for visible fluorescence photography. The filter 31c has spectral characteristics shown in FIG. 6B. The filter 31c may be used for fundus-auto-fluorescence (FAF), by which the fundus is irradiated with second wavelength laser beam (laser beam in the visible range). The auto-fluorescence photography explained herein by way of example utilizes the principle that lipofuscin in the retinal pigment epithelium exhibits auto-fluorescence (wavelength of around 500 nm to around 750 nm) upon irradiation with second light (wavelength of around 490 nm). It is also possible to photograph the fundus by exciting a fluorescence substance other than the above example by providing a light source and a filter in accordance with the fluorescence characteristics of the fluorescence substance from which light emission is desired.

The opening portion 31d is disposed at the photography region Lz when aligning the examinee's eye E and the device, or during normal fundus observation. At this time, the opening portion 31d passes almost all of the light from the fundus Er and guides the light to the light receiving device 25. In the first embodiment, the size of the opening portion 31d is designed to substantially correspond to the size of the photography region Lz of the light receiving optical system 4.

Figure 7:
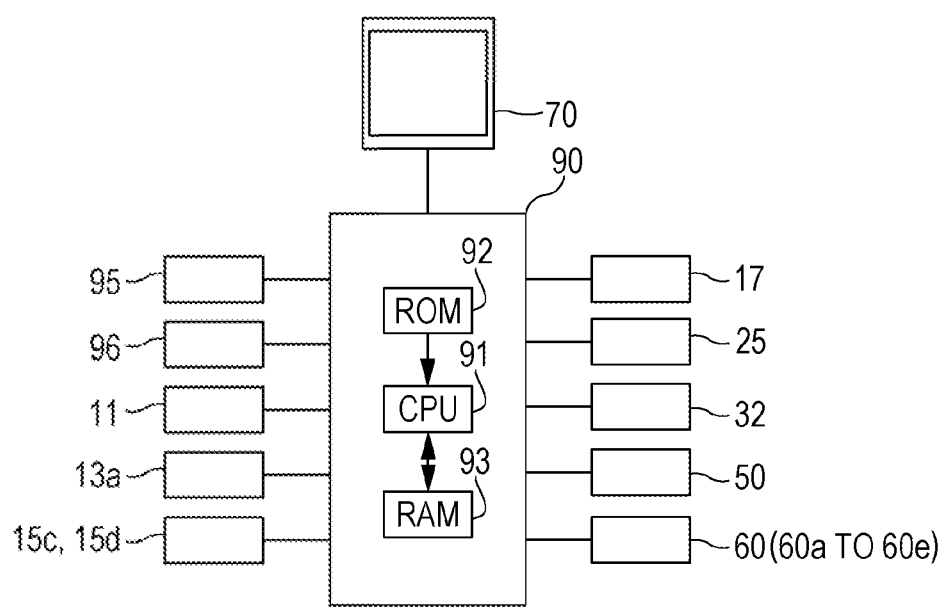
FIG. 7 is a block diagram illustrating an electrical configuration of the ophthalmologic photographing apparatus.
Figure 8:
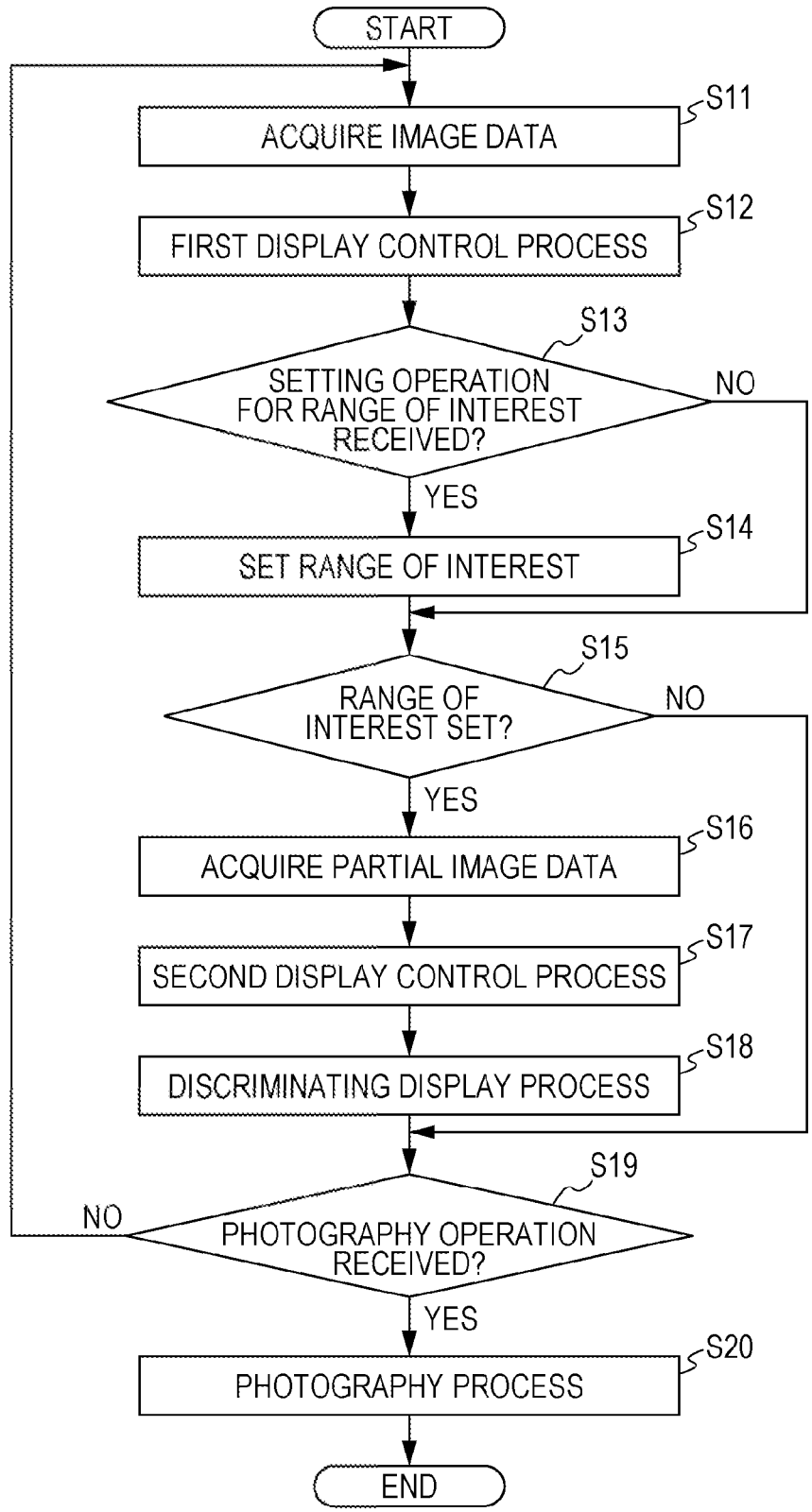
FIG. 8 is a flowchart of a photography display process executed by a CPU.
Figure 9:
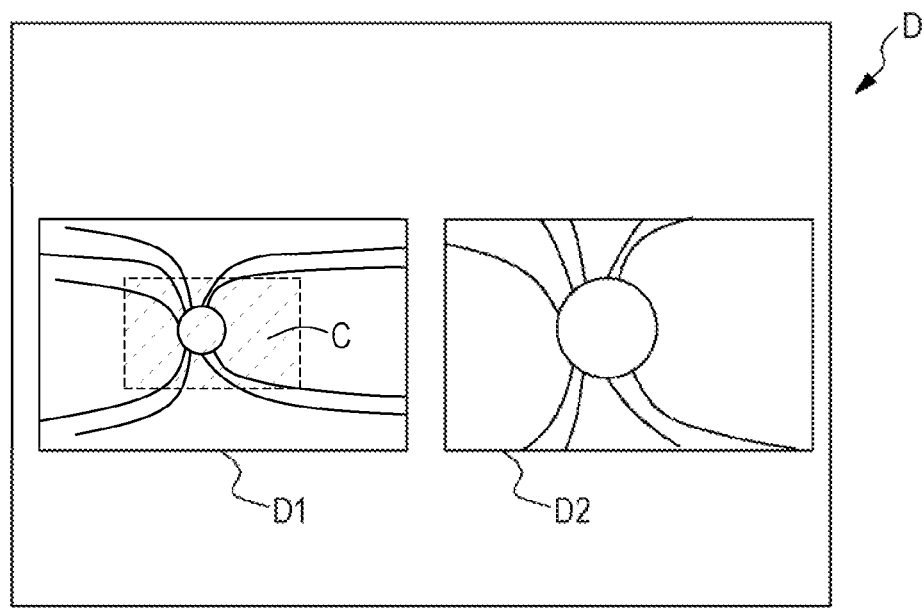
FIG. 9 is a schematic diagram of an example of the manner of display of fundus image.

FIG. 7 is a block diagram of a control system for the ophthalmologic photographing apparatus 1 of the first embodiment. Major control of the ophthalmologic photographing apparatus 1 is performed by a control unit 90. The control unit 90 is a processing device (ophthalmic image processing apparatus) including an electronic circuit for performing a control process for each unit of the ophthalmologic photographing apparatus 1 and a measurement result computation process.

In the first embodiment, the control unit 90 is connected to a hard disk (HDD) 95, an image process IC 96, the laser beam emitting portion 11, the drive mechanism 13a, a resonant scanner drive motor 15c, a galvanometer mirror drive motor 15d, the lens moving mechanism 17, the light receiving device 25, the pulse motor 32, the drive mechanism 50, an operating unit 60, and a monitor (display medium, display device) 70, and the like.

The control unit 90 is also provided with a CPU (display control unit, photographing view angle adjustment mechanism) 91, a ROM 92, and a RAM (storage unit) 93. The CPU 91 is a processing device for executing various processes relating to the ophthalmologic photographing apparatus 1. The ROM 92 is a non-volatile storage device in which a control program, fixed data, and the like are stored. The RAM 93 is a rewritable, volatile storage device. In the RAM 93, there is stored temporary data used for the photography and measurement of the examinees eye E by the ophthalmologic photographing apparatus 1, for example.

The HDD 95 is a rewritable, non-volatile storage device. In the HDD 95, there is stored at least a program for causing the control unit 90 to execute a photography display process which will be described later. In the HDD 95, a photographed fundus image (fundus photography image) is stored by the ophthalmologic photographing apparatus 1.

The image process IC 96 is a processing device configured to generate image data of the fundus image photographed using the photographing optical system 2, based on a light receiving signal from the light receiving device 25. When the fundus Er is scanned two-dimensionally with laser beam, the light receiving device 25 successively receives the fundus reflected light corresponding to the laser beam scan position on the fundus Er. As a result, the light receiving signal is successively output from the light receiving device 25 to the image process IC 96. In the image process IC 96 according to the first embodiment, the input light receiving signal is converted into image data, and the image data is accumulated in a buffer, which is not shown. Thus, when the light receiving signal for one frame (one fundus image) is input to the image process IC 96, the image data for the one frame is accumulated in the buffer of the image process IC 96.

The operating unit 60 is provided with an input device, such as a switch, operated by the examiner. In the first embodiment, the input device includes various switches, such as a joystick 60a, a photography switch 60b, a photographing view angle change-over switch 60c, and a photography mode selection switch 60d.

The joystick 60a is an input device operated by the examiner to designate the photographing range of the fundus Er. The control unit 90 drives the drive mechanism 50 in accordance with the operation of the joystick 60a to move the ophthalmologic photographing apparatus 1 with respect to the examinee's eye E. Thus, the position adjustment of the photographing optical system 2 may be performed by the control unit 90 driving the drive mechanism 50. Alternatively, the ophthalmologic photographing apparatus 1 may be provided with a drive mechanism that receives a manual input from the examiner. Namely, the drive mechanism is a mechanism for the examiner to perform position adjustment of the photographing optical system 2 by manually moving the position of the photographing optical system 2.

The photography switch 60b is a switch operated to photograph (capture) the fundus image.

The photographing view angle change-over switch 60c is a switch operated to switch the photographing view angle (photographing range) of the photographing optical system 2. In the first embodiment, the size of the photographing range is selected by the examiner from at least two ranges (the first view angle and the second view angle) via the photographing view angle change-over switch 60c. The control unit 90 locates each lens included in the objective lens optical system 16 in accordance with the operation of the photographing view angle change-over switch 60c. In the first embodiment, when the first view angle is selected, the control unit 90 drives the lens moving mechanism 17 so that each lens of the objective lens optical system 16 is set at the location shown in FIG. 2A. On the other hand, when the second view angle is selected, the control unit 90) drives the lens moving mechanism 17 so that each lens of the objective lens optical system 16 is set at the location shown in FIG. 2B. Thus, in the first embodiment, the lenses 16a to 16c of the objective lens optical system 16 are located such that the position of the pivot point is maintained between when the photographing view angle is the first view angle and when the angle is the second view angle.

The photography mode selection switch 60d is a switch for switching the photography mode of the ophthalmologic photographing apparatus 1 executed by the control unit 90 among a manual photography mode, a FAF photography mode, and an IGC photography mode. While the details will be described later, the manual mode is a mode for observing the fundus using the fundus reflected light of infrared light. The FAF photography mode is a mode for observing auto-fluorescence emitted from the fundus Er. The IGC photography mode is a mode for observing fluorescence from the fluorescence contrast agent given to the fundus Er. When the photography mode selection switch 60d is operated, the wavelength of the light output from the laser beam emitting portion 11, and the barrier filter set in the optical axis passing region are switched in accordance with the newly set photography mode.

The monitor 70 is a display device including a display for displaying an image of the examinee's eye E photographed by the ophthalmologic photographing apparatus 1, and various measurement results.

The operation of the ophthalmologic photographing apparatus 1 having the above-described configuration will be described.

First, the examiner selects the manual photography mode by operating the photography mode selection switch 60d. The control unit 90 drives the pulse motor 32 to adjust the rotation angle of the rotating plate 31 so that the opening portion 31d of the rotating plate 31 is positioned on the optical axis L2. Also, when the manual photography mode is selected, the control unit 90 sets the photographing optical system 2 in a lighted state such that the laser beam emitting portion 11 emits the laser beam (infrared light) of the first wavelength. In this way, the examiner can perform the subsequent positioning of the photographing optical system 2 while looking at the image photographed using the fundus reflected light. Use of the image photographed using the fundus reflected light makes recognition of the photography state easier than in the case of a fluorescence photography image, assisting the examiner in performing the positioning in a preferable manner.

The examiner then aligns the photographing optical system 2 and photographs a photography image using the ophthalmologic photographing apparatus 1. While not shown in the drawings, in the first embodiment, the scanning unit 15 is continuously driven by the control unit 90 at least until the alignment process is executed and photography of the image is completed. Namely, the fundus Er is continuously scanned with laser beam according to a predetermined procedure.

The examiner then performs observation of the live image (fundus observe image) photographed using the fundus reflected light, and causes the device to acquire the photography image. The operation of the ophthalmologic photographing apparatus 1 in this case will be described with reference to a flowchart of FIG. 8. The live image herein includes not only the fundus image displayed simultaneously with the timing of photography (i.e., in real-time), but also a fundus image displayed after a slight lag (such as on the order of several milliseconds or several seconds) from the timing of photography.

In the ophthalmologic photographing apparatus 1 according to the first embodiment, the photography and display of the fundus image is performed by the photography display process. In the photography display process, initially, the process of S11 and S12 is executed by the CPU 91. Thus, the fundus image photographed by the ophthalmologic photographing apparatus 1 is displayed in a display region D of the monitor 70.

In the process of S11, the CPU 91 acquires from the image process IC 96 the image data of one frame of the fundus image (S11). For example, in the first embodiment, the image data is acquired by transferring the image data accumulated in the buffer of the image process IC 96 to the RAM 93. The present process stands by until the one frame of the image data is accumulated in the buffer of the image process IC 96.

Then, the CPU 91 executes a first display control process (S12). In the first display control process (S12), the CPU 96 displays the one frame of the fundus image newly acquired by the ophthalmologic photographing apparatus 1 in a first display region D1 (see FIG. 9). As will be described below, the present process is executed repeatedly until the photographing of the fundus photography image is completed. As a result, in the first display region D1, live images (observation image, first live image) including continuous fundus images are successively displayed by the first display control process (S12). Thus, the examiner can adjust the position of the photographing optical system 2 so as to obtain a desired photography image by operating the joystick 60a while confirming the display content in the first display region D1. In the first embodiment, the moving process for the photographing optical system 2 (drive control of the drive mechanism 50) which is performed in accordance with the operation of the joystick 60a may be performed by the control unit 90 in parallel with the photography display process. Alternatively, the moving process for the photographing optical system 2 may be a process, not illustrated, which is executed in the control unit 90 as needed during the stand-by time for acquiring the image data from the image process IC 96.

The number of pixels (the so-called "number of image pixels") of the fundus image acquired by the process of S11 may be greater than the number of pixels (the so-called "number of device pixels") in the first display region D1 of the monitor 70. In this case, in the first display process (S12), the CPU 91 may execute a process of compressing (reducing) the fundus image in accordance with the number of pixels in the first display region D1.

The CPU 91 then executes a process for displaying a part of the fundus image displayed in the first display region D1 (second partial image) in a different region from the first display region D1 (S13 to S17).

First, the CPU 91 determines whether an operation for setting a range C of interest has been received (S13). The range C of interest refers to the range in which an image process is performed in the fundus image displayed in the first display region D1 (or in the region of the fundus Er indicated by the fundus image). The operation for setting the range C of interest may be performed by, for example, designating the position on the fundus image where the examiner wishes to set the range C of interest, using a pointing device or the like, such as a mouse. In the first embodiment, the setting of the range C of interest includes moving the set position of the range C of interest and modifying the vertical and horizontal sizes of the range C of interest, as well as newly providing the range C of interest.

In the first embodiment, it is determined in S13 that the setting operation for the range C of interest is not received until the setting operation for the range C of interest is performed by the examiner for the first time (S13: No). In this case, the CPU 91 executes the process of S15 without setting the range C of interest.

On the other hand, when it is determined in the process of S13 that the setting operation for the range C of interest is received (S13: Yes), the CPU 91 sets the range C of interest to the range designated by the examiner through the setting operation (S14). For example, in the first embodiment, the CPU 91 stores in the RAM 93 position information indicating the position that the range C of interest occupies in the fundus image photographing range. Then, the CPU 91 executes the process of S15.

Thus, in the first embodiment, the range C of interest is described as being provided upon instruction from the examiner. However, the setting of the range C of interest is not limited to the above. For example, regardless of instruction from the examiner, the CPU 91 may set the range C of interest to a predetermined range of the fundus image. Further, in the first embodiment, it is described that the CPU 91 sets, in accordance with an instruction from the examiner with regard to not just whether the range C of interest is to be provided but also the position and size and the like of the range C of interest. However, the setting of the range C of interest is not limited to the above. For example, the ophthalmologic photographing apparatus 1 (or CPU 91) may be configured to constantly set the range C of interest to a constant position (such as the center region of the fundus image) with respect to the fundus image.

In the process of S15, the CPU 91 determines whether the range C of interest is provided (S15). As described above, if the setting operation for the range C of interest is performed at least once, the range C of interest is already provided. In this case, the CPU 91 executes the process of S16 (S15: Yes).

In the process of S16, the CPU 91 acquires the image data of the second partial image (S16). In the first embodiment, the image data of the second partial image is generated and acquired by the CPU 91 extracting data indicating the range of interest from the image data indicating the entire fundus image. In the first embodiment, the CPU 91 can extract the image data of the second partial image on the basis of the position information of the range C of interest acquired in advance from the image data indicating the entire fundus image by the process of S14.

The CPU 91 then executes a second display control process (S17). In the second display control process (S17), the CPU 91 displays the second partial image of which the image data has been acquired by the process of S16 in a second display region D2 (see FIG. 9). As in the first display control process (S12), the second display control process is repeatedly executed until the photographing of the fundus photography image is completed. Thus, by the second display control process (S17), second live images including continuous second partial images are displayed in the second display region D2.

Namely, the CPU 91 displays the first live images and the second live images side by side on the monitor 70.

In the first embodiment, the second live images are described as being synchronized with the first live images. However, the manner of display is not limited to the above. The manner of display may include, for example, a manner such that the first live image or the second live image is continuously displayed while the other display and a non-display are switched at intervals of several seconds. The first live image and the second live image may be alternatively displayed.

Namely, the CPU 91 may be configured to display at least one of the first live image and the second live image on the monitor 70.

In the second display control process (S17) according to the first embodiment, the CPU 91 displays the second live image enlarged larger than the range C of interest on the first live image. For example, in the first embodiment, the second live image is displayed in the second display region D2 having the same size as the first display region D1 in which the fundus image is displayed (see FIG. 9). In this way, the examiner can observe the range C of interest even more easily using the second live image.

As described above, there may be the case where the number of pixels (the number of image pixels) of the fundus image acquired by the ophthalmologic photographing apparatus 1 is greater than the number of pixels (the number of device pixels) in the first display region D1, where a compressed image of the fundus image acquired by the ophthalmologic photographing apparatus 1 is displayed as the first live image. In such a case, in the second display control process (S17), the second live image may be displayed with a higher resolution than the first live image. The "resolution" referred to in the first embodiment is correlated with the fundus tissue resolution in the image. In this case, the range C of interest in the fundus image is displayed in greater detail in the second display region D2 than in the first display region D1. Accordingly, the examiner can perform detailed observation of the range C of interest in a preferable manner.

The CPU 91 then executes a discriminating display process (S18). The process of S18 is executed so that, when the second live image is being displayed in the second display region D2, the range C of interest and other regions are displayed on the first live image in a discriminating manner. The manner of the discriminating display is not particularly limited as long as the display assists discrimination by the examiner between the range C of interest and other regions. In the first embodiment, as an example of the discriminating display, the range C of interest is enclosed by lines in the first display region D1 (on the first live image) (see FIG. 9). Other manners of the discriminating display may include a manner in which the range C of interest is displayed more darkly or lightly than the surrounding region, and a manner in which the range C of interest is provided with hatching.

Then, the CPU 91 determines whether a photography operation for the photography image (in the first embodiment, the operation of the photography switch 60b) is received (S19). If the photography operation is not received (S19: No), the CPU 91 repeatedly executes the process from S11 to S19. On the other hand, if the photography operation by the examiner is received in the process of S19 (S19: Yes), the CPU 91 executes the photography process of S20. In the photography process (S20), the CPU 91 acquires the fundus photography image. This photography process may include a process in which the CPU 91 newly acquires a fundus image from the image process IC 96, and stores the acquired fundus image in the HDD 95 or the like as the fundus photography image. From the image process IC, a plurality of fundus images may be acquired. Alternatively, the fundus photography image may include an averaged image and the like of a plurality of continuously photographed fundus images. In the first embodiment, after the photography process (S20), the photography display process ends.

Referring back to the process of S15, if the setting operation for the range C of interest has not been performed even once, in the process of S15, the CPU 91 determines that the range C of interest is not set. In this case, the CPU 91 performs the process of S19 and thereafter while skipping the process of S16 to S18. Thus, the second live image is not displayed in the display region D until the setting operation for the range C of interest is performed by the examiner.

In the foregoing description, the case has been described in which the photography image photographed using the fundus reflected light is acquired. Alternatively, a photography image photographed using fluorescence from the fundus may be acquired. In this case, the examiner, while looking at the observation image (first live image and second live image) photographed using the fundus reflected light, operates the photography mode selection switch 60d when the positioning of the photographing optical system 2 is performed, and switches the photography mode to the photography mode using fluorescence from the fundus (FAF photography mode, IGG photography mode), for example. Thereafter, the examiner operates the photography switch 60b.

As described above, in the ophthalmologic photographing apparatus 1 according to the first embodiment, the first live image including a plurality of continuous fundus images is displayed on the monitor 70 by the first display control process (S12) which is successively executed. In this way, the examiner's failure to confirm a feature area (such as the optic disc, macula, a lesioned part, or a blood vessel) present in the photographing range of the fundus image can be reduced. Further, in the ophthalmologic photographing apparatus 1 according to the first embodiment, when the setting operation for the range C of interest with respect to the fundus image is performed by the examiner beforehand, the second partial image extracted from the fundus image as a range of interest is generated by the second display control process (S17). The second live image including a plurality of continuous second partial images is also displayed on the monitor 70. As a result, the examiner can observe, easily and in detail, the feature area present in a part (in the first embodiment, range C of interest) of the fundus image which is displayed as the second live image. Thus, in the ophthalmologic photographing apparatus 1, the examiner can easily observe the photographing range of the fundus image thoroughly and in detail, using the live image of the fundus image.

For example, if the position of the pivot point of the laser beam is displaced from the pupil position of the examinee's eye E, some of the light from the device may be blocked by the iris (eclipsed by the iris). In this case, the outer edge portion and the like of the fundus image may be subjected to the influence of the light eclipsed by the iris. This may lead to the examiner's confirmation failure if only the second live image including a part of the fundus image is displayed. Thus, if the examiner acquires the photography image of the fundus image as a whole through confirmation of only the second live image, there may be obtained a fundus image such that the outer edge portion and the like is hard to observe. In the ophthalmologic photographing apparatus 1 according to the first embodiment, the first live image including the fundus image is displayed together with the second live image. Thus, the examiner can easily confirm whether the outer edge portion and the like of the fundus image are subjected to the influence of light eclipsed by the iris. Accordingly, the examiner, while confirming the first and second live images, can have the device execute the photography image acquisition for acquiring the desired photography image with the photographing optical system 2 positioned. In this way, in the ophthalmologic photographing apparatus 1 according to the first embodiment, the fundus image photography can be performed in a preferable manner.

Further, in the ophthalmologic photographing apparatus 1 according to the first embodiment, the range C of interest of the fundus image from which the second partial image is extracted is set based on the instruction from the examiner (S14). The range desired by the examiner in the fundus image can be displayed as the second live image. Thus, the examiner can perform the fundus observation in an even more preferable manner.

Further, in the ophthalmologic photographing apparatus 1 according to the first embodiment, when the second live image is displayed in the second display region D2, the range C of interest and the other regions are displayed on the first live image in the first display region D1 in a discriminating manner (S18). In this way, the examiner can readily understand the corresponding relationship between the fundus image and the second partial image.

The first embodiment has been described with reference to the case where the range C of interest is set at a constant position with respect to the display range (or the photographing range) of the fundus image. For example, in the ophthalmologic photographing apparatus 1 of the first embodiment, the position of the range C of interest on the first display region D1 is not varied before and after the photographing range of the optical system in the fundus Er is modified by the alignment operation. However, the range C of interest may not be set at the constant position with respect to the display range of the fundus image. For example, the range C of interest may be set at a constant position on the fundus Er indicated in the fundus image. In this case, for example, when the photographing range in the fundus Er is moved by a fine involuntary movement of the examinee's eye E during fixation or the like, the range C of interest on the first display region D tracks the constant position on the fundus Er. For example, the first embodiment may be modified as follows. In this modification, the CPU 91 may perform the setting process for the range C of interest by acquiring a template image from a part of the fundus image (S14). As the template image, an image extracted from the fundus image acquired in advance by the ophthalmologic photographing apparatus 1 may be used.

The CPU 91 also identify, from the fundus image displayed in the first display region D1 at each timing, an image region having high correlation with the template image. In this way, movement of the image region extracted as the second display region D2 is detected. In accordance with the detection result, the CPU 91 may correct the region extracted as the second partial image from the fundus image, and perform the second display control process (S17) in the corrected region. In this way, even when the photographing range in the fundus Er is moved by the fine involuntary movement of the examinees eye E during fixation or the like, a constant area included in the template image is displayed in the second display region D2.

Next, a second embodiment of the present disclosure will be described with reference to FIGS. 10 to 13. As described above, the ophthalmologic photographing apparatus 1 according to the first embodiment displays a plurality of continuous live images in the first display region D1 of the monitor 70. The ophthalmologic photographing apparatus 1 also displays the second live image including the second partial image of the fundus image displayed in the first display region D1 in the second display region D2 of the monitor 70.

Meanwhile, the ophthalmologic photographing apparatus 100 according to the second embodiment acquires a first fundus image and a second fundus image having mutually different image resolutions, and displays a combined image of the first fundus image and the second fundus image on the monitor 70. In the second embodiment, the first fundus image is a fundus image photographed with the photographing view angle of the photographing optical system 2 being set at the second view angle (i.e., in the wide-angle photography mode). The second fundus image (first partial image) is an image photographed with regard to a part of the first fundus image with the photographing view angle of the photographing optical system 2 being set at the first view angle (i.e., in the narrow-angle photography mode).

As mentioned above, the first fundus image and the second fundus image are formed on the basis of the light receiving signal from the same light receiving device (the light receiving device 25 in the present embodiment). In the second embodiment, the wide-angle first fundus image may be an image photographed at a photographing view angle of 100° or more and 180° or less (more preferably, not more than 120°). The narrow angle second fundus image may be an image photographed at a photographing view angle of 30° or more and 75° or less (preferably 40° or more and 55° or less). In the second embodiment, the second fundus image has all the higher resolution for the decrease in the photographing view angle compared with the first fundus image. In the following description, the observation image and the photography image of the first fundus image will be referred to as an observation image (wide) and a photography image (wide), respectively, and the observation image and the photography image of the second fundus image will be referred to as an observation image (narrow) and a photography image (narrow), respectively.

The ophthalmologic photographing apparatus 100 according to the second embodiment includes, for example, the same optical system as the ophthalmologic photographing apparatus 1 according to the first embodiment. The ophthalmologic photographing apparatus 100 may also include substantially the same control system as the control system of the ophthalmologic photographing apparatus 1 according to the first embodiment. However, the ophthalmologic photographing apparatus 100 differs from the ophthalmologic photographing apparatus 1 of the first embodiment at least in the control program defining the process executed at the time of fundus image photography.

Figure 10:
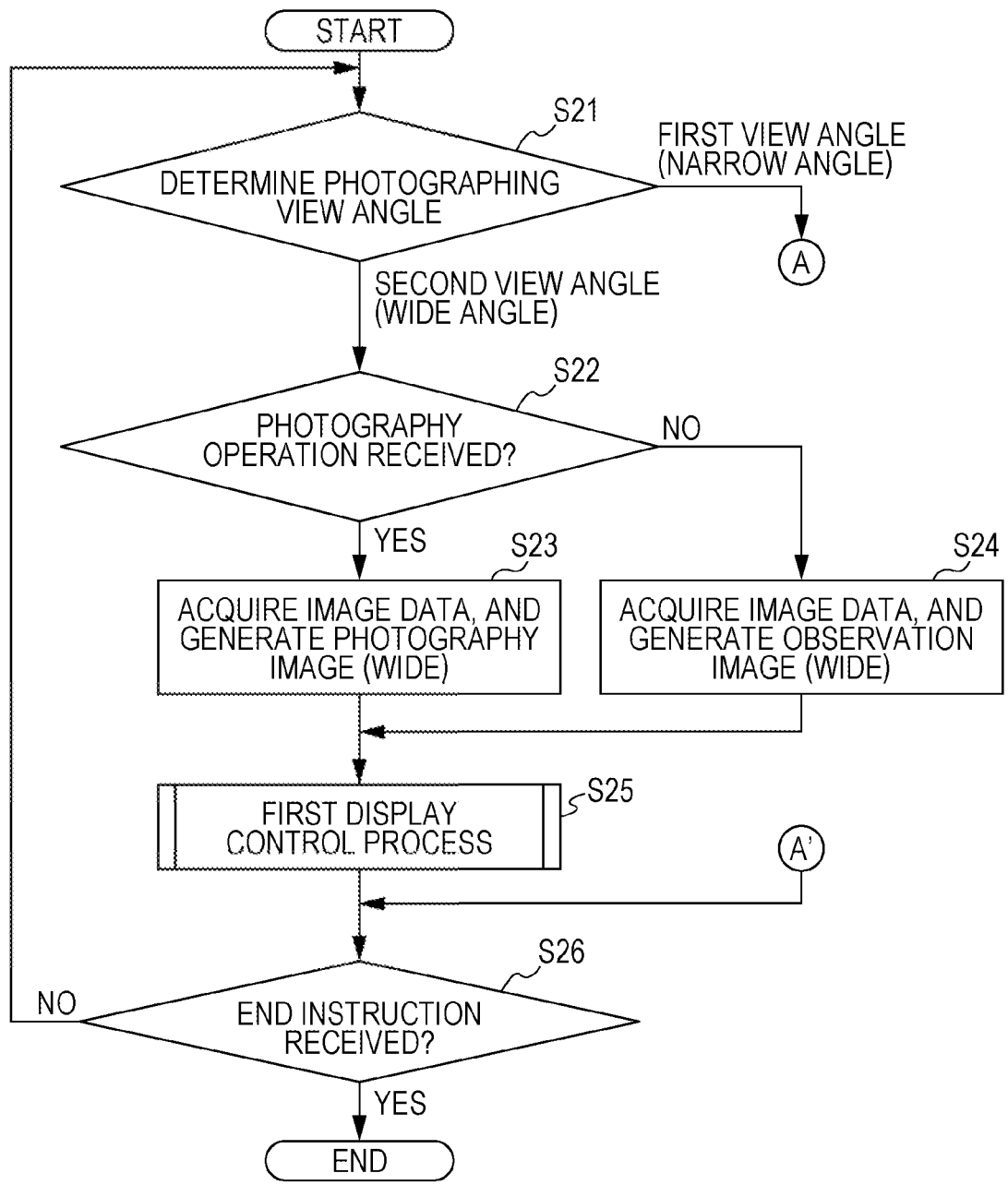
FIG. 10 is a flowchart of the photography display process according to a second embodiment.
Figure 11:
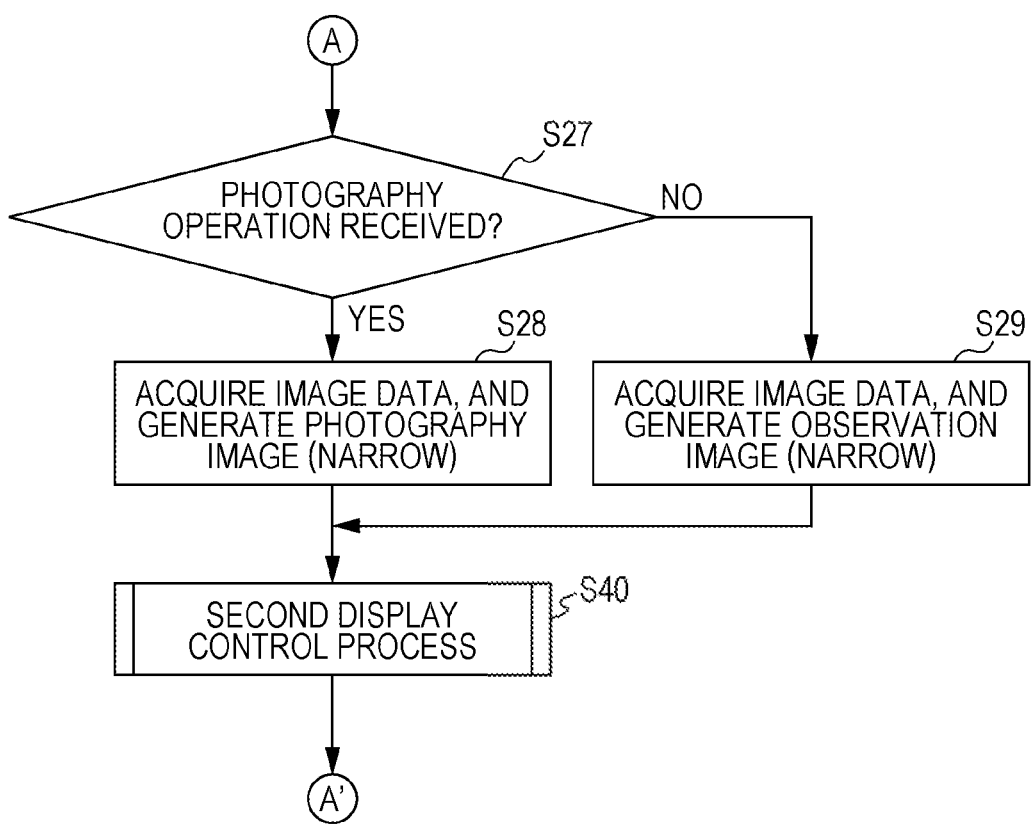
FIG. 11 is a subsequent flowchart of FIG. 10.
Figure 12:
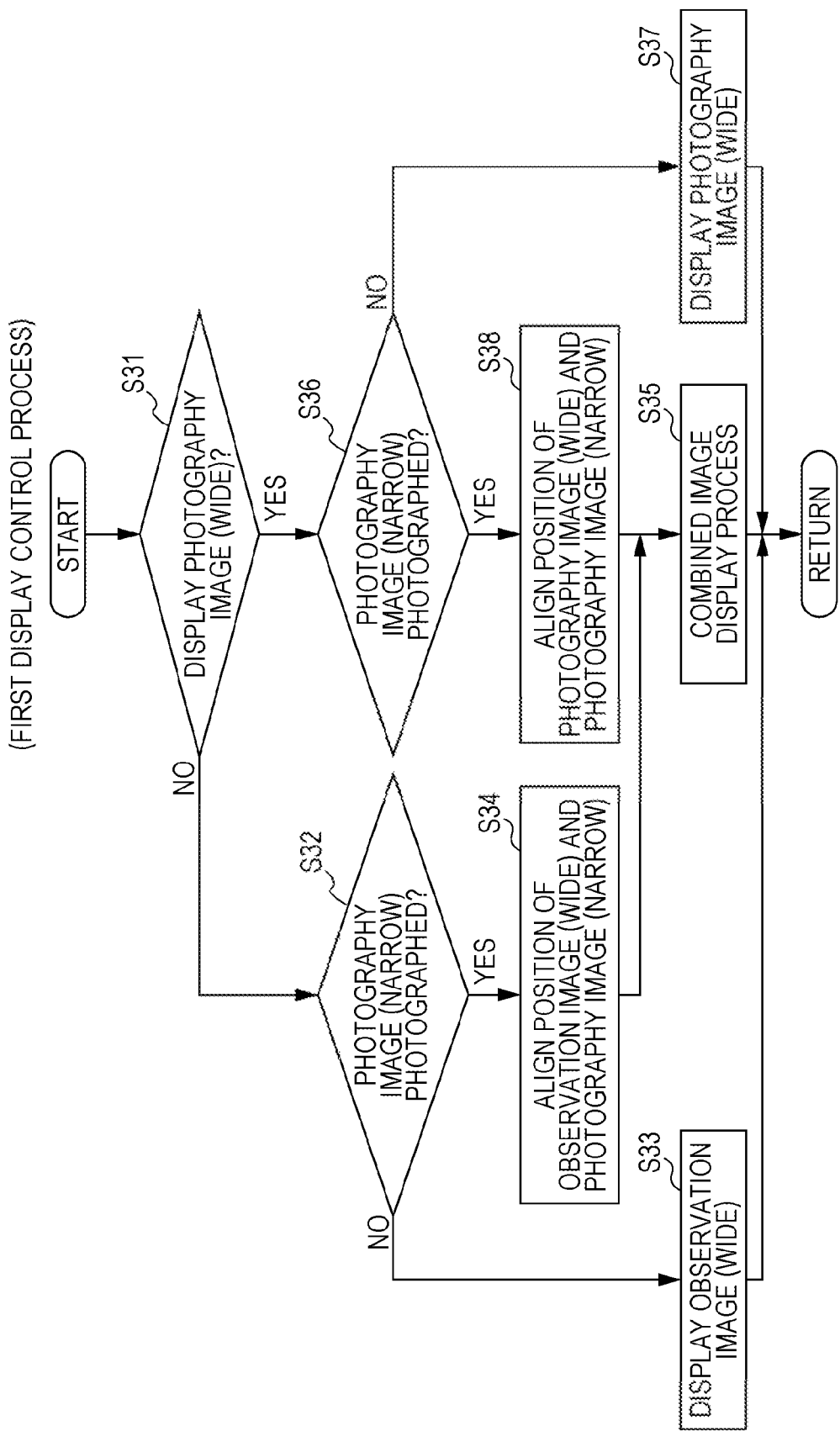
FIG. 12 is a flowchart of a first display control process in the second embodiment.
Figure 13:
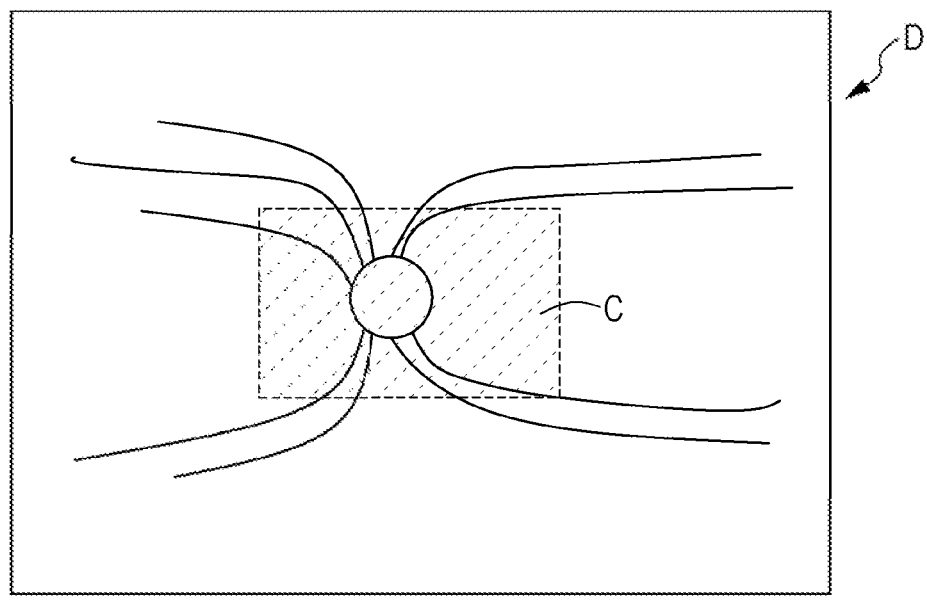
FIG. 13 is a schematic diagram of an example of a manner of display of fundus image in the second embodiment.

In the following, with reference to flowcharts of FIG. 10 to FIG. 12, the operation of the ophthalmologic photographing apparatus 100 at the time of fundus image photography will be described.

First, the CPU 91 determines whether the photographing view angle of the photographing optical system 2 (photographing magnification) is the first view angle or the second view angle wider than the first view angle (S21). For example, in the second embodiment, the CPU 91 implements this determination on the basis of the photographing view angle (photographing magnification, optical magnification) that is set in advance in accordance with the operation of the photographing view angle change-over switch 60c.

If it is determined that the photographing view angle is the second view angle (S21: second view angle), the CPU 91 executes the process of S22 and thereafter in the wide-angle photography mode. By the process of S22, the CPU 91 determines whether a photography operation is received (S22). If it is determined that the photography operation is received (S22: Yes), the CPU 91 acquires one frame of image data from the image process IC 96 (S23). Thus, the image data of the fundus image of the wide view angle (second view angle in the second embodiment) is acquired. The image data is displayed as the photography image (wide) on the monitor 70 by the subsequent process. In the second embodiment, the image data of the photography image (wide) acquired by the process of S23 is temporarily stored in the RAM 93 until a photography image (wide) is newly photographed. The CPU 91 may also save the image data of the photography image acquired by the process of S23 in the non-volatile storage device (such as the HDD 95). After the process of S23, the CPU 91 executes the first display control process (S25).

On the other hand, if it is determined that the photography operation is not receive (S21: No), the CPU 91 acquires one frame of the image data from the image process IC 96 (S24). The image data is displayed as the observation image (wide) on the monitor 70 by the subsequent process (S24). In the second embodiment, the image data of the observation image (wide) acquired by the process of S24 is stored in the temporarily RAM 93 until photography of the observation image (wide) is newly performed. After the process of S23, the CPU 91 executes the first display control process (S25).

In the wide-angle photography mode, display control for the monitor 70 is performed in the first display control process (S25). In the first display control process (S25), the CPU 91, using the image data acquired by the process of S23 or the process of S24, controls the display on the monitor 70 (S25). With reference to FIG. 12, the first display control process (S25) in the wide-angle photography mode will be described. In the first display control process (S25), initially, the CPU 91 determines whether the photography image (wide) is to be displayed (S31). In the second embodiment, if the photography image (wide) is acquired in advance by the process of S23, the CPU 91 determines that the photography image (wide) is to be displayed (S3: Yes). On the other hand, if the photography image (wide) is not acquired in advance, the CPU 91 determines that the photography image (wide) is not to be displayed (S31: No). If, by the process of S31, it is determined that the photography image (wide) is not to be displayed (S31: No), a display process of the monitor 70 is performed using the image data of the observation image (wide) acquired by the immediately preceding process of S24. Namely, in this case, a live image including the observation image (wide) is displayed. At this time, in the second embodiment, the CPU 91 determines whether a photography image (narrow) is photographed (acquired) in the narrow-angle photography mode in advance (S32).

If the photography image (narrow) is not acquired in advance (S32: No), the CPU 91 displays the observation image (wide) in the display region D of the monitor 70 (S33).

On the other hand, if the photography image (narrow) is acquired in advance (S32: Yes), the CPU 91 performs positioning of the observation image (wide) and the photography image (narrow) (S34). In the second embodiment, the CPU 91 can perform the position alignment (matching process) of the first fundus image (observation image (wide) or the photography image (wide)) and the second fundus image (observation image (narrow) or the photography image (narrow)) by, for example, utilizing the correlation relationship of the images (such as pattern matching). In this way, even when the positional relationship of the photographing range between the first fundus image and the second fundus image is not constant because of a fine involuntary movement during fixation or the like, an image process for the both images, which will be described below, can be properly performed. When the second fundus image is included at a constant position in the first fundus image, the CPU 91 may perform the image positioning on the basis of information indicating the photographing range of the second fundus image (i.e., the range C of interest) in the first fundus image.

Namely, the CPU 91 can correct displacement between the images by matching an image region corresponding to the second fundus image on the fundus image and the second fundus image through an image process.

In the second embodiment, the first fundus image and the second fundus image are photographed at the same number of pixels, although their photographing view angles are different from each other. Thus, in the second embodiment, when the positioning of the first fundus image and the second fundus image is performed, the enlarging/reducing magnification ratio for each of the first fundus image and the second fundus image is adjusted by the CPU 91. For example, in the second embodiment, with respect to an enlarged image of the first fundus image where the range C of interest in the first fundus image corresponds to the size of the second fundus image, positioning of the second fundus image is performed. The enlarging/reducing magnification ratio for each of the first fundus image and the second fundus image may be determined from the photographing view angle (or photographing magnification) of the first fundus image and the photographing view angle (or photographing magnification) of the second fundus image, for example.

After completion of the positioning process of S34, the CPU 91 executes a combined image display process (S35). In the combined image display process (S35), the CPU 91 displays a combined image obtained by combining, by image processing, the first fundus image and the second fundus image that have been positioned beforehand, on the monitor 70. In the second embodiment, the CPU 91 displays a combined image of an enlarged image of the first fundus image used for positioning and the second fundus image on the monitor 70. The image processing for combining the first fundus image and the second fundus image may utilize various image processing techniques. For example, the combined image may be acquired by addition of the first fundus image and the second fundus image. Alternatively, the range C of interest of the first fundus image may be substituted by the second fundus image.

Referring back to the process of S31, in the second embodiment, even when it is determined that the photography image (wide) is to be displayed (S31: Yes), the CPU 91 determines whether the photography image (narrow) is acquired in advance (S36). If the photography image (narrow) is not acquired in advance (S36: No), the CPU 91 displays the photography image (wide) stored in the RAM 93 in the display region D of the monitor 70 (S38). On the other hand, if the photography image (narrow) is acquired in advance (S31: Yes), the CPU 91 performs position alignment between the photography image (wide) and the photography image (narrow) (S38), and displays a combined image of the photography image (wide) and the photography image (narrow) in the display region D (S35). Thus, in the second embodiment, when the photography image (wide) is stored in the RAM 93 in advance, the photography image (wide) in the RAM 93 is used for the first image portion of the combined image. Accordingly, in the second embodiment, when the photography image of the first fundus image is acquired in advance using the photographing optical system 2, the photography image is continuously displayed in the first fundus image portion of the combined image.

The CPU 91 may not only display the combined image of the photography image (wide) and the photography image (narrow) on the monitor 70, but also print the combined image on a printing medium using a printer and the like, thus producing a display on the printing medium.

In the process of S26, the CPU 91 determines whether the present process is to be ended (S26). For example, the CPU 91 ends the present process when an instruction for ending the process is received from the examiner (S30: Yes). On the other hand, when it is determined that the process is not to be ended (S30: No), the CPU 91 repeats the process from S21.

Referring back to S21, if it is determined that the photographing view angle is the first view angle (S21: first view angle), the CPU 91 executes the process in the narrow-angle photography mode (S27 to S29, S40).

First, the CPU 91 executes the process of S27 to S29, and acquires the second fundus image (observation image (narrow) or photography image (narrow)). Initially, the CPU 91 determines whether the photography operation is received (S27). If it is determined by the CPU 91 that the photography operation is received (S27: Yes), the CPU 91 acquires from the image process IC 96 one frame of the image data as the image data of the photography image (narrow) (S28). The image data of the photography image (narrow) is temporarily stored in the RAM 93 until a new photography image (narrow) is photographed. After the process of S28, the CPU 91 executes the second display control process (S40).

On the other hand, if it is determined by the CPU 91 that the photography operation is not received (S27: No), the CPU 91 acquires from the image process IC 96 one frame of the image data as the image data of the photography image (narrow) (S29). Thus, the image data of the fundus image of the narrow view angle (in the second embodiment, the first view angle) is acquired. The image data of the observation image (narrow) is temporarily stored in the RAM 93 until a new observation image (narrow) is photographed. After the process of S23, the CPU 91 executes the second display control process (S40).

In the narrow-angle photography mode, display control for the monitor 70 is performed by the second display control process (S40). In the second display control process (S40), the display of the monitor 70 is controlled using the image data of the second fundus image acquired in the process of S28 or S29. In the second control process (S40) according to the second embodiment, a process based on each process of the first display control process (S25) is performed. Specifically, in the second control process (S40), the process of the flowchart of FIG. 12 is executed where in each step, the photography image (wide) and the photography image (narrow) are mutually replaced, and the observation image (wide) and the observation image (narrow) are mutually replaced. After the second control process (S40) is executed, the CPU 91 returns to FIG. 10 and executes the process of S26.

By the ophthalmologic photographing apparatus 100 according to the second embodiment, when one of the first fundus image (fundus image) and the second fundus image (first partial image) is acquired (photographed) in advance, the CPU 91, upon newly acquiring (photographing) the other image, displays the combined image of the first fundus image and the second fundus image in the display region D of the monitor 70. The combined image is created by combining the second fundus image with the image region of the first fundus image corresponding to the second fundus image (in the second embodiment, range C of interest) by image processing. In the second embodiment, the combined image has the same photographing view angle as the first fundus image. Thus, the examiner can observe a wide area of the fundus through the combined image. The second fundus image also has a higher image resolution than the first fundus image. Thus, the combined image is displayed on the monitor 70 with the image resolution of the second fundus image portion in the combined image being higher than the image resolution of the first fundus image portion. Thus, the examiner can observe the fundus Er in detail through the region of the combined image in which the second fundus image is combined. Further, in the combined image, the second fundus image is combined with the image region of the first fundus image corresponding to the second fundus image. Thus, the examiner can easily perform observation. Accordingly, the image processing device according to claim 1 enables the examiner to recognize the state of the fundus Er in a preferable manner through the combined image displayed on the monitor 70.

In the second embodiment, the display with the image resolution of the second fundus image portion being higher than the image resolution of the first fundus image portion may be performed when the combined image as a whole is displayed on the monitor 70 at a default display magnification ratio. Alternatively, the display may be performed when the combined image as a whole is displayed at a higher magnification ratio than the default display magnification ratio. For example, when the number of device pixels in the display region D is greater than the number of pixels of the image in at least the first fundus image portion, the second fundus image portion may be displayed at a higher resolution than in the first fundus image portion in the overall display of the combined image as a whole.

The display with the image resolution of the second fundus image portion being higher than the image resolution of the first fundus image portion may be performed when a part or whole of the combined image is displayed on the monitor 70 at a higher magnification ratio than the default display magnification ratio. In this case, the CPU 91 displays the combined image at least at two display magnification ratios of a first display magnification ratio and a second display magnification ratio greater than the first display magnification ratio.

When modifying the display magnification ratio from the first display magnification ratio to the second display magnification ratio greater than the first display magnification ratio, the CPU 91 displays the second fundus image portion of the combined image at a higher resolution than in the case of the first display magnification ratio. In this case, the CPU 91 may set the display region with the first display magnification ratio and the display region with the second display magnification ratio side by side on the same screen. In this case, for example, the CPU 91 may display the combined image of the first display magnification ratio and the second fundus image of the second display magnification ratio side by side in the same screen.

The CPU 91 may be configured to switch the display among combined images of a plurality of display magnification ratios in a single display region. In this case, the CPU 91, when the region in the combined image where the second fundus image is combined is displayed at the second display magnification ratio, displays the combined image (or the region in the combined image where the second fundus image is combined) at a higher resolution than when a peripheral region (i.e., the first fundus image region) of the combined image where the second fundus image is not combined is displayed at the second display magnification ratio.

In the ophthalmologic photographing apparatus 100 according to the second embodiment, when the combined image is generated in the first display control process (S25) or the second display control process (S40), position alignment (matching) between the first fundus image and the second fundus image is performed. As a result, in the ophthalmologic photographing apparatus 100, a proper combined image can be obtained Further, in the ophthalmologic photographing apparatus 100 according to the second embodiment, the second fundus image is combined by image processing with an enlarged image of the first fundus image such that the range C of interest in the first fundus image corresponds to the size of the second fundus image. In this way, each area of the fundus can be displayed on the combined image while suppressing the hiding of each area of the fundus included in the photographing range of the fundus image by the second fundus image. Thus, the examiner can thoroughly observe the feature area of the fundus through the combined image.

Further, by the ophthalmologic photographing apparatus 100), the CPU 91 displays as a live image one of the first fundus image and the second fundus image that corresponds to the photographing view angle of the photographing optical system 2 (optical magnification) set by the CPU 91 or the lens moving mechanism 17.

In the ophthalmologic photographing apparatus 100, when the observation image of one of first fundus image and the second fundus image that corresponds to the photographing view angle of the photographing optical system 2 is photographed, if the photography image of the other image is acquired in advance, the photography image and the live image including the one image are combined by the CPU 91 and then displayed on the monitor 70. In this way, the examiner can observe the first fundus image and the second fundus image virtually in real-time through the combined image.

Namely, the CPU 91 combines, of the first fundus image and the second fundus image, the other image acquired in advance at a photographing view angle different from the photographing view angle of the photographing optical system 2 (optical magnification) set by the CPU 91 or the lens moving mechanism 17, with the live image of the one image and displays the combined image.

In the ophthalmologic photographing apparatus 100 according to the second embodiment, the case has been described in which both the first fundus image and the second fundus image forming the combined image are photographed using the fundus reflected light from the fundus. Alternatively, at least one of the first fundus image and the second fundus image may be a fluorescence image photographed using fluorescence from the fundus.

In the second embodiment, the case has been described in which the two fundus images (the first fundus image and the second fundus image) with different view angles are photographed by switching the location of the objective lens optical system 16. However, the technique for acquiring the two fundus images with different view angles is not limited to the above. For example, the two fundus images with different view angles may be photographed by adjusting the swing angle of the scanning unit 15 of the photographing optical system 2 (the resonant scanner 15a and the galvanometer mirror 15b in the embodiments). At this time, the scan speed of the scanning member may be delayed when photographing the second fundus image compared with when photographing the first fundus image. In this way, at the time of photography of the second fundus image, the number of pixels acquired by the scan per unit length of the fundus Er can be made greater than at the time of photography of the first fundus image. Thus, in such device, the effect similar to that of the second embodiment can be obtained. In the second embodiment, the switching of the photographing view angle may be performed by attaching or detaching a wide-angle lens attachment for increasing the photographing view angle of the device, instead of switching the lens arrangement of the objective lens optical system 16.

In the second embodiment, the case has been described in which the combined image of the first fundus image and the second fundus image (first partial image) is created by the ophthalmologic photographing apparatus 1. However, the technique for creating the combined image is not necessarily limited to the above. For example, the combined image may be created by a general-purpose computer (such as a personal computer). In this case, there may be prepared (stored) in a computer hard disk and the like an analyze program for causing a processor of the computer to execute the process of S34 and S35 of the photography display process executed by the ophthalmologic photographing apparatus 1 of the embodiment. In this case too, as in the ophthalmologic photographing apparatus 1 according to the embodiment, the combined image of the first fundus image and the second fundus image (first partial image) can be created.

In the foregoing embodiments, the case has been described in which the common light receiving device 25 is used when the fundus image is photographed using the reflected from the fundus Er and when the fundus image is photographed using fluorescence produced in the fundus Er. Alternatively, different light receiving devices 25 may be used for each case. For example, the optical path of the light receiving optical system 4 may be branched by a half mirror or the like, and a light receiving device may be provided at the end of each optical path, so that photography can be performed simultaneously using respective light receiving devices. As the respective light receiving devices, elements having different light receiving characteristics may be disposed, whereby photography can be simultaneously performed at a plurality of wavelengths.

In the foregoing embodiment, the control unit 90 has been described as performing position control for each lens of the objective lens optical system 16. However, the technique for setting the position of each lens is not limited to the above. For example, the lens moving mechanism 17 configured to mutually link the location of each lens of the objective lens optical system 16 may maintain the laser beam pivot point during modification of the photographing view angle in the photographing optical system 2.

Further, in the above embodiments, the case has been described in which the objective lens optical system 16 includes two lenses (first convex lens 16a, second convex lens 16b). However, the objective lens optical system 16 may include three or more lenses. In an example of the objective lens optical system 16 including three lenses, a lens with a negative power may be provided in addition to the first convex lens 16a and the second convex lens 16b closer to the scanning unit 15 than the second convex lens 16b. For example, as illustrated in FIGS. 14A and 14B, a concave lens 16c may be provided as the lens with a negative power.

Figure 14A:
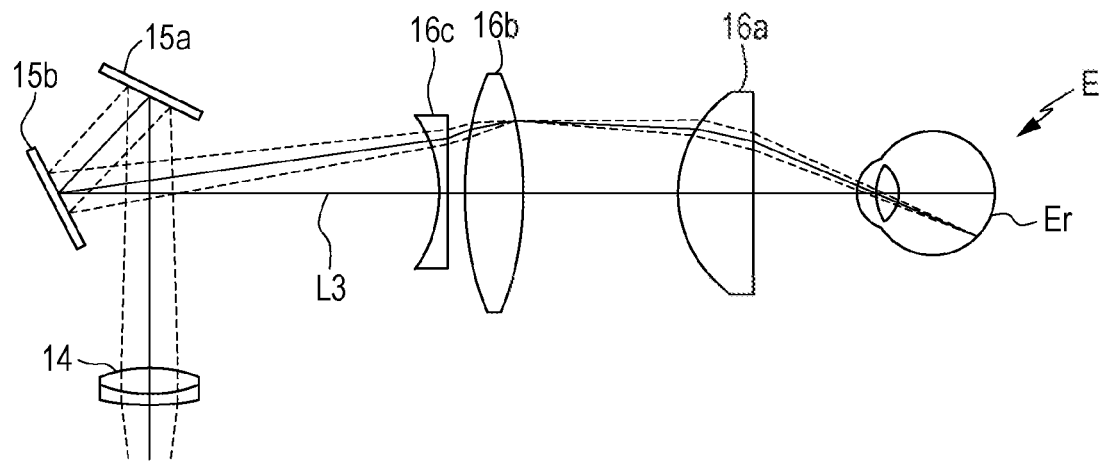
FIG. 14A illustrates a lens arrangement in a narrow-angle photography mode in a modification of the objective lens optical system.
Figure 14B:
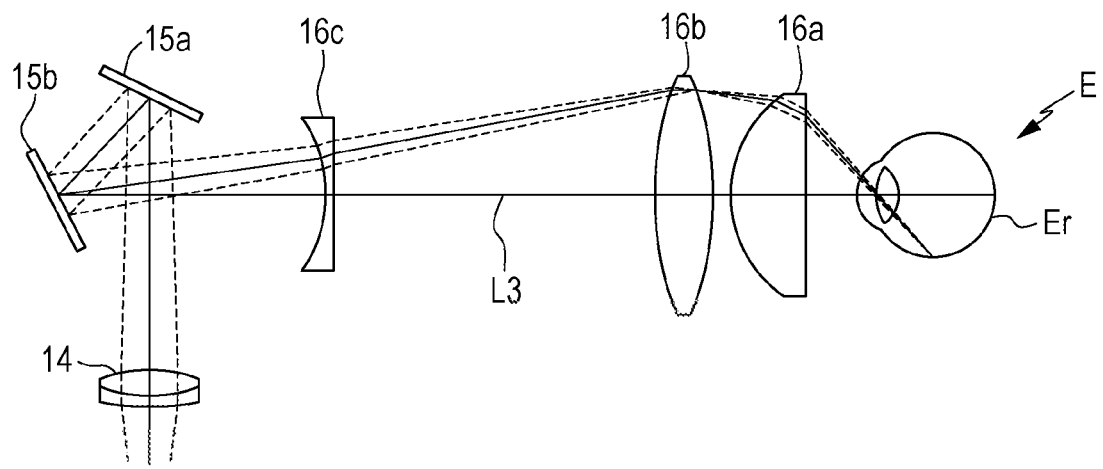
FIG. 14B is a schematic diagram of a lens arrangement in a wide-angle photography mode.

In the example of FIGS. 14A and 14B, the concave lens 16c is disposed with the concave surface facing the scanning unit 15. Further, in the example of FIGS. 14A and 14B, the concave lens 16c includes a piano-concave lens. However, the concave lens 16c is not limited to the above. For example, the concave lens 16c may include a bi-concave lens, a concave meniscus lens, an aspherical lens, or a compound lens.

The concave lens 16c with the concave surface facing the scanning unit causes the laser beam from the scanning unit 15 that passes through the concave lens 16c other than the center thereof to be refracted away from the optical axis L3 compared with when in the absence of the concave lens 16c. Thus, the laser beam height can be set to a required height at a position closer to the scanning unit 15 than when in the absence of the concave lens 16c. Namely, when the constant photographing view angle is obtained, each of the two convex lenses 16a and 16b can be located at a position closer to the scanning unit 15 than when the concave lens 16c is not provided. Accordingly, in the example of FIGS. 14A and 14B, the total length of the objective lens optical system 16 can be reduced compared with when the concave lens 16c is not provided, enabling the ophthalmologic photographing apparatus 100 to have a compact configuration.

In the example of FIGS. 14A and 14B, the two convex lenses 16a and 16b are displaced by the lens moving mechanism 17 in the same way as in the example of FIGS. 2A and 2B when the photographing view angle of the photographing optical system 2 is the first view angle (see FIG. 14A) and when it is the second view angle (see FIG. 14B). At this time, the concave lens 16c may be displaced together with the two convex lenses 16a and 16b. For example, the two convex lenses 16a and 16b as well as the concave lens 16c may be disposed by the lens moving mechanism 17 such that the position of the pivot point with respect to the examinee's eye and the diopter scale can be maintained when the photographing view angle is the first view angle and when it is the second view angle.

As described above, when the objective lens optical system 16 include the two convex lenses 16a and 16b, the position of the pivot point with respect to the examinee's eye and the diopter scale are not maintained before and after the photographing view angle switching except when the photographing view angle is switched between the specific view angles corresponding to the design values of the two convex lenses 16a and 16b (see FIG. 4, for example). On the other hand, in the example of FIGS. 14A and 14B, a change in the diopter scale due to displacement of the two convex lenses 16a and 16b can be cancelled out by displacement (movement) of the concave lens 16c. Thus, in the example of FIGS. 2A and 2B, a good fundus image can be more readily photographed even when the photographing view angle is not switched between the specific view angles. The position of the concave lens 16c may be determined as needed on the basis of the focal point distance of each of the lenses 16a to 16c, and the required photographing view angle and the like. The concave lens 16c may be fixedly disposed on the optical axis L3.

Figure 15:
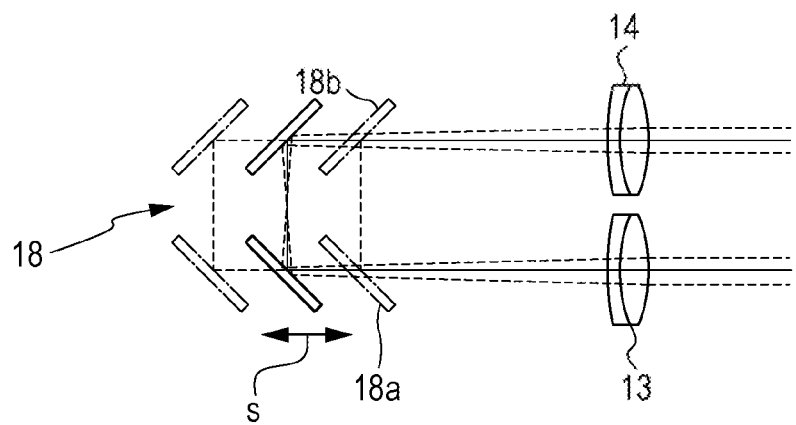
FIG. 15 illustrates an example of a diopter scale correction portion.

In the configuration of the foregoing embodiments, the diopter scale correction portion may be disposed on the common optical path of the light projecting optical system 3 and the light receiving optical system 4 (such as between the scanning unit 15 and the laser beam emitting portion 11). The diopter scale correction portion has the function of correcting a change in the diopter scale of the objective lens optical system 16 due to the photographing view angle, or the function of correcting the diopter scale error of the examinee's eye E with respect to the emmetropic eye. As a specific example, the diopter scale correction portion 18 will be described with reference to FIG. 15. The diopter scale correction portion 18 performs diopter scale correction by adjusting the optical path length of the photographing optical system 2 between the scanning unit 15 and the laser beam emitting portion 11. The diopter scale correction portion 18 may include two mirrors 18a and 18b and a driving part which is not shown. The driving part moves the two mirrors 18a and 18b in an arrow direction s while maintaining the positional relationship of the two mirrors 18a and 18b. As a result, the optical path length of the common portion of the light projecting optical system 3 and the light receiving optical system 4 is modified.

In the foregoing embodiments, the case has been described in which, in order to modify the photographing view angle such that the position of the pivot point with respect to the examinee's eye is maintained, the first convex lens 16a and the second convex lens 16b are displaced in the mutually same direction along the optical axis L3. However, the displacement of the first convex lens 16a and the second convex lens 16b is not limited to the above. When the photographing view angle is switched while maintaining the position of the pivot point with respect to the examinee's eye, at least the second convex lens 16b may be displaced along the optical axis L3 in a direction corresponding to an increase or a decrease in the photographing view angle. More specifically, when the photographing view angle is increased, at least the second convex lens 16b may be displaced in a direction from the scanning unit 15 toward the examinee's eye E. When the photographing view angle is narrowed, at least the second convex lens 16b may be displaced in a direction from the examinee's eye E toward the scanning unit 15. In this case, depending on the design value of the objective lens optical system 16 and on the value of the required photographing view angle (the first photographing view angle and the second photographing view angle), the first convex lens 16a may be displaced not just in the same direction as the second convex lens 16b but also an opposite direction to the second convex lens 16b.

In the foregoing embodiments, the case has been described in which the photographing view angle in the photographing optical system 2 is switched to the two stages of the first view angle and the second view angle greater than the first view angle. However, the photographing view angle in the photographing optical system 2 may be switched to more than two stages. The photographing view angle may be switched continuously rather than in a step-wise manner. In these cases, the technology of the foregoing embodiments may be applied when the photographing view angle is modified between arbitrary two values.

In the foregoing embodiments, the ophthalmologic photographing apparatus 1 has been described as being an SLO device that scans the fundus two-dimensionally with laser beam. However, the configuration of the ophthalmologic photographing apparatus 1 is not limited to the above. For example, the ophthalmologic photographing apparatus (fundus photographing apparatus) 1 may include a so-called line scan SLO. In this case, the fundus is scanned one-dimensionally with a linear laser beam flux in accordance with the operation of the scanning unit 15. The ophthalmologic photographing apparatus 1 may also include a fundus camera.

The present disclosure may also relate to a scanning laser ophthalmoscope configured to photograph the fundus of the examinee's eye.

The ophthalmic image processing apparatus according to the embodiments may be expressed as the following devices.

A first ophthalmic image processing apparatus includes a photographing optical system configured to photograph a fundus image by projecting light to the fundus of the examinee's eye and receiving light from the fundus as a result of the projected light with a light receiving device, the display control unit generating the fundus image and a second partial image extracted from a part of the fundus image based on a light receiving signal from the light receiving device, and causing a first live image including a plurality of continuous fundus images and a second live image including a plurality of continuous second partial images to be displayed side by side on the display device.

A second ophthalmic image processing apparatus is the first ophthalmic image processing apparatus wherein the display control unit causes the second live image to be displayed while being enlarged larger than a region of the first live image that corresponds to the part of the fundus image.

A third ophthalmic image processing apparatus is the first ophthalmic image processing apparatus wherein the display control unit displays a range of the fundus image that is determined in accordance with an instruction from an examiner as the second partial image.

A fourth ophthalmic image processing apparatus is the first ophthalmic image processing apparatus wherein the display control unit performs a discriminating display of the region corresponding to the part of the fundus image extracted as the second partial image and another region in the first live image.

A fifth ophthalmic image processing apparatus includes a photographing optical system configured to photograph a fundus image by projecting light to the fundus of the examinee's eye and receiving light from the fundus as a result of the projected light with a light receiving device, the display control unit causing the display device to display the fundus image photographed using the photographing optical system and a second partial image photographed for a range of interest included in the fundus image, and causing at least one of the fundus image and the second partial image to be displayed as a live image.

A sixth ophthalmic image processing apparatus includes a storage unit configured to store a fundus image and a first partial image which is a partial image photographed for a part of the fundus image and which has a higher resolution than the fundus image, and a display control unit configured to combine the first partial image with respect to an image region of the fundus image corresponding to the first partial image, and to cause a display medium to display a combined image of the fundus image and the first partial image.

A seventh ophthalmic image processing apparatus is the first ophthalmic image processing apparatus wherein the display control unit is configured to display a part or whole of the combined image at a first display magnification ratio and a second display magnification ratio greater than the first display magnification ratio, wherein, when a first partial image region where the first partial image is combined in the combined image is displayed at the second display magnification ratio, a peripheral region where the first partial image is not combined in the combined image is displayed at a higher resolution than when displayed at the second display magnification ratio.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. An ophthalmic image processing apparatus comprising:
a storage unit configured to store a fundus image and a first partial image, the first partial image being a partial image photographed for a part of the fundus image and having a higher resolution than the fundus image; and
a display control unit configured to combine the first partial image with respect to an image region on the fundus image corresponding to the first partial image, and to display a combined image of the fundus image and the first partial image on a display medium;
a photographing optical system configured to photograph the fundus by projecting light to the fundus of the examinee's eye and receiving light from the fundus as a result of the light projection using a light receiving device, the photographing optical system being configured to photograph the fundus image and the first partial image by setting a photographing view angle of the photographing optical system using a photographing view angle adjustment mechanism;
wherein:
the display medium is a display; and
the display control unit displays one of the fundus image and the first partial image that corresponds to the optical magnification set by the photographing view angle adjustment mechanism as a live image.

2. The ophthalmic image processing apparatus according to claim 1, wherein:
the display control unit is configured to display a part or whole of the combined image at a first display magnification ratio and a second display magnification ratio greater than the first display magnification ratio; and
the display control unit, when a first partial image region where the first partial image is combined in the combined image is displayed at the second display magnification ratio, displays the combined image at a higher resolution than when a peripheral region where the first partial image is not combined in the combined image is displayed at the second display magnification ratio.

3. The ophthalmic image processing apparatus according to claim 1, wherein the display control unit displays the combined image and an enlarged image of the first partial image side by side on the display medium.

4. The ophthalmic image processing apparatus according to claim 1, wherein the display control unit further matches an image region of the fundus image corresponding to the first partial image with the first partial image by image processing, and corrects displacement between the images.

5. The ophthalmic image processing apparatus according to claim 4, wherein the display control unit adjusts an enlarging/reducing magnification ratio of the fundus image and the first partial image such that a size of an image region of the fundus image corresponding to the first partial image corresponds to a size of the first partial image, and then generates the combined image by the image processing.

6. The ophthalmic image processing apparatus according to claim 1, wherein the display control unit combines the other image of the fundus image and the first partial image that is acquired in advance at a photographing view angle different from the photographing view angle set by the photographing view angle adjustment mechanism with the live image of the one image, and displays the combined image.

7. The ophthalmic image processing apparatus according to claim 1, wherein at least one of the fundus image and the first partial image is a fluorescence image photographed using fluorescence from the fundus.

8. An ophthalmic image processing apparatus comprising:
a photographing optical system configured to photograph a fundus image by projecting light to the fundus of an examinee's eye and receiving light from the fundus as a result of the light projection using a light receiving device; and
a display control unit configured to generate the fundus image and a second image that is a partial image extracted from the fundus image, based on a light receiving signal from the light receiving device, and to display a first live image including a plurality of continuous fundus images and a second live image including a plurality of continuous second partial images side by side on a display medium.

9. The ophthalmic image processing apparatus according to claim 8, wherein the display control unit displays the second live image enlarged larger than a region corresponding to the partial image of the fundus image in the first live image.

10. The ophthalmic image processing apparatus according to claim 8, wherein the display control unit displays a range determined by an instruction from an examiner in the fundus image as the second image.

11. The ophthalmic image processing apparatus according to claim 8, wherein the display control unit performs a discriminating display of a region corresponding to the partial image of the fundus image extracted as the second image and another region on the first live image.

12. The ophthalmic image processing apparatus according to claim 8, wherein the fundus image is a front fundus image.

13. The ophthalmic image processing apparatus according to claim 12, wherein the front fundus image is a scanning laser ophthalmoscope image.

14. The ophthalmic image processing apparatus according to claim 8, wherein a photographing view angle of the fundus image is smaller than a photographing view angle of the second image.

15. An ophthalmic image processing apparatus comprising:
a photographing optical system configured to photograph a fundus image by projecting light to the fundus of an examinee's eye and receiving light from the fundus as a result of the light projection using a light receiving device; and
a display control unit configured to display the fundus image photographed using the photographing optical system and a second image photographed for a range of interest included in the fundus image on a display medium, the second image being a partial image of the fundus image, and to display at least one of the fundus image and the second partial image as a live image.

16. The ophthalmic image processing apparatus according to claim 15, wherein the fundus image is a front fundus image.

17. The ophthalmic image processing apparatus according to claim 16, wherein the front fundus image is a scanning laser ophthalmoscope image.

18. The ophthalmic image processing apparatus according to claim 15, wherein a photographing view angle of the fundus image is smaller than a photographing view angle of the second image.

19. The ophthalmic image processing apparatus according to claim 15, wherein each of the fundus image and the second image is generated based on a light receiving signal from the light receiving device of the photographing optical system.

* * * * *